US009187484B2

(12) United States Patent
Galemmo, Jr. et al.

(10) Patent No.: US 9,187,484 B2
(45) Date of Patent: Nov. 17, 2015

(54) TRIAZOLOPYRIDAZINE COMPOUNDS, USE AS INHIBITORS OF THE KINASE LRRK2, AND METHODS FOR PREPARATION THEREOF

(71) Applicants: Southern Research Institute, Birmingham, AL (US); THE UAB RESEARCH FOUNDATION, Birmingham, AL (US)

(72) Inventors: Robert A. Galemmo, Jr., San Francisco, CA (US); Andrew B. West, Birmingham, AL (US); Joseph A. Maddry, Birmingham, AL (US); Subramaniam Ananthan, Birmingham, AL (US); Ashish Kumar Pathak, Birmingham, AL (US); Jacob Valiyaveettil, Hoover, AL (US)

(73) Assignees: Southern Research Institute, Birmingham, AL (US); The UAB Research Foundation, Birmingham, AL (US)

( * ) Notice: Subject to any disclaimer, the term of this patent is extended or adjusted under 35 U.S.C. 154(b) by 0 days.

(21) Appl. No.: 13/875,751

(22) Filed: May 2, 2013

(65) Prior Publication Data

US 2013/0296298 A1 Nov. 7, 2013

Related U.S. Application Data

(60) Provisional application No. 61/641,364, filed on May 2, 2012.

(51) Int. Cl.

| | |
|---|---|
| ***A61K 31/50*** | (2006.01) |
| ***A61K 31/501*** | (2006.01) |
| ***C07D 487/00*** | (2006.01) |
| ***C07D 487/04*** | (2006.01) |
| ***A61K 31/5025*** | (2006.01) |

(52) U.S. Cl.

CPC .......... *C07D 487/04* (2013.01); *A61K 31/5025* (2013.01)

(58) Field of Classification Search

None

See application file for complete search history.

(56) References Cited

U.S. PATENT DOCUMENTS

| | | | |
|---|---|---|---|
| 3,903,086 | A | 9/1975 | Berger et al. |
| 3,928,342 | A | 12/1975 | Berger et al. |
| 3,989,832 | A | 11/1976 | Berger et al. |
| 6,440,967 | B1 | 8/2002 | Block et al. |
| 2004/0192696 | A1 | 9/2004 | Green et al. |
| 2008/0312225 | A1 | 12/2008 | Schmidt et al. |
| 2010/0099683 | A1 | 4/2010 | Tomkinson et al. |

FOREIGN PATENT DOCUMENTS

| | | | | |
|---|---|---|---|---|
| DE | 20 30 218 | A1 | 12/1971 | |
| DE | 21 09 577 | A1 | 9/1972 | |
| DE | 22 02 744 | A1 | 7/1973 | |
| DE | 22 02 745 | A1 | 7/1973 | |
| EP | 1 481 977 | A1 | 12/2004 | |
| WO | WO-99/37303 | A1 | 7/1999 | |
| WO | WO 2004058769 | * | 7/2004 | ........... C07D 487/04 |
| WO | WO-2008/030744 | A2 | 3/2008 | |
| WO | WO-2008/069500 | A1 | 6/2008 | |
| WO | WO-2008/124838 | A1 | 10/2008 | |
| WO | WO-2011/141756 | A1 | 11/2011 | |

OTHER PUBLICATIONS

Pollak, et. al., Tetrahedron (1966), 22(7), 2073-9.*

National Center for Biotechnology Information. PubChem Compound Database; CID=43935799, http://pubchem.ncbi.nlm.nih.gov/compound/43935799 (accessed Apr. 9, 2015).*

National Center for Biotechnology Information. PubChem Compound Database; CID=7190386, http://pubchem.ncbi.nlm.nih.gov/compound/7190386 (accessed Apr. 9, 2015).*

International Search Report and Written Opinion dated Sep. 12, 2013.

Chen et al., "Synthesis, structures of novel zinc and copper compounds based on pyridazino[3,2-c]1,2,4-triazole derivatives", Journal of Molecular Structure, vol. 920, No. 1-3, Feb. 28, 2009, pp. 342-349.

Legraverend et al., "Synthesis of S-TriazoloA4,3-Bupyridazine C-Nucleosides (1)", Journal of Heterocyclic Chemistry, vol. 18, No. 5, Jan. 1981, pp. 893-898.

Supplementary European Search Report issued Aug. 19, 2015 in EP Appln. No. 13784613.

* cited by examiner

*Primary Examiner* — Jeffrey H Murray

(74) *Attorney, Agent, or Firm* — Novak Druce Connolly Bove + Quigg LLP

(57) ABSTRACT

Provided are novel LRRK2 kinase inhibitors and methods of treating disease states using these inhibitors. Examples of LRRK2 kinase inhibitors are compounds of the formula:

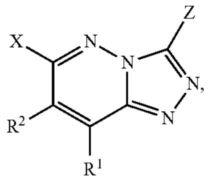

or derivatives thereof. An example is 1-(piperidin-1-yl)-2-((3-(thiophen-2-yl)-[1,2,4]triazolo[4,3-b]pyridazin-6-yl)thio)butan-1-one. Particular uses include treating neurodegenerative diseases, cancer, autoimmune diseases and leprosy.

7 Claims, No Drawings

TRIAZOLOPYRIDAZINE COMPOUNDS, USE AS INHIBITORS OF THE KINASE LRRK2, AND METHODS FOR PREPARATION THEREOF

CROSS REFERENCE TO RELATED APPLICATION

This application claims the benefit of U.S. Provisional Application No. 61/641,364 filed on May 2, 2012, the entire contents of which are hereby incorporated by reference.

TECHNICAL FIELD

The present disclosure is concerned with certain triazolopyridazine compounds that are capable of inhibiting certain protein kinases, and especially the leucine-rich repeat kinase 2 (LRRK2) protein. Compounds of the present disclosure can be used to treat a number of disorders caused by or associated with abnormal LRRK2 kinase activity. Compounds of the present disclosure can be used to treat disorders including neurodegenerative diseases such as Parkinson's disease; precancerous conditions and cancer; autoimmune disorders such as Crohn's disease, rheumatoid arthritis and psoriasis; and leprosy (Hansen's disease).

BACKGROUND ART

The LRRK2 gene encodes a protein kinase and it has been disclosed that missense mutations in this gene can lead to a number of diseases such as various neurodegenerative diseases including Parkinson's disease. Additionally, LRRK2 is genetically linked to precancerous conditions and cancer; autoimmune disorders such as Crohn's disease, rheumatoid arthritis and psoriasis; and leprosy. For instance, it has been suggested that certain mutations in LRRK2 can lead to Parkinson's disease through the up-regulation of the kinase activity of the protein kinase. It is suspected that this protein kinase may be over-active in Parkinson's disease.

There has been much interest raised by the recent discovery that different autosomal dominant point mutations within the gene encoding for LRRK2 predispose humans to develop late-onset Parkinson's disease (OMIM accession number 609007), with a clinical appearance indistinguishable from idiopathic Parkinson's disease. See Paisan-Ruiz et al. (2004), "Cloning of the gene containing mutations that cause PARK 8-linked Parkinson's disease." Neuron. 44, 595-600; Mata et al. (2006), "LRRK2 in Parkinson's disease: protein domains and functional insights." Trends Neurosci. 29, 286-293; Taylor et al. (2006), "LRRK2: a common pathway for Parkinsonism, pathogenesis and prevention?" Trends Mol. Med. 12, 76-82. The genetic analysis undertaken to date indicates that mutations in LRRK2 are relatively frequent, not only accounting for 5-10% of familial Parkinson's disease, but also being found in a significant proportion of sporadic Parkinson's disease cases. See Farrer et al. (2005), "LRRK2 mutations in Parkinson disease." Neurology 65, 738-740; and Zabetian et al. (2005), "A clinic-based study of the LRRK2 gene in Parkinson disease yields new mutations." Neurology 65, 741-744.

Little is known about how LRRK2 is regulated in cells, what its physiological substrates are and how mutations cause or increase risk of Parkinson's disease. The domain structure of LRRK2 is depicted in WO 2011/141756 A1, disclosure of which is incorporated herein by reference. See FIG. 1 therein, which also shows mutations which have been reported in patients with Parkinson's disease. The defining feature of the LRRK2 enzyme is a leucine rich repeat (LRR) motif (residues 1010-1291), a Ras-like small GTPase (residues 1336-1510), a region of high amino acid conservation that has been termed the C-terminal of Ras complex (COR) domain (residues 1511-1878), a protein kinase catalytic domain (residues 1879-2132) and a C-terminal VVD40 motif (2231-2276). See Bosgraaf et al. (2003), "Roc, a Ras/GTPase domain in complex proteins." Biochim. Biophys. Acta. 1643, 5-10; and Marin (2006), "The Parkinson disease gene LRRK2: evolutionary and structural insights." Mol. Biol. Evol. 23, 2423-2433.

The protein kinase domain of LRRK2 belongs to the tyrosine-like serine threonine protein kinases and is most similar to the kinase RIP (Receptor Interacting Protein), which play key roles in innate immunity signaling pathways. See Manning et al. (2002), "The protein kinase complement of the human genome." Science 298, 1912-1934. Almost 40 single amino acid substitution mutations have been linked to autosomal-dominant Parkinson's disease. Mata et al., supra; Taylor et al., supra; WO 2011/141756 A1. It has also been reported that the most prevalent mutant form of LRRK2 accounting for approximately 6% of familial Parkinson's disease and 3% of sporadic Parkinson's disease cases in Europe, comprises an amino acid substitution of Gly2019 to a Ser residue. Gly2019 is located within the conserved DYG-Mg'-binding motif, in subdomain-VII of the kinase domain. Mata et al., supra. More recent reports suggest that this mutation enhances the autophosphorylation of LRRK2, as well as its ability to phosphorylate myelin basic protein 2-3-fold. West et al. (2005), "Parkinson's disease-associated mutations in leucine-rich repeat kinase 2 augment kinase activity." Proc. Natl. Acad. Sci. USA 102, 16842-16847; and Greggio et al. (2006), "Kinase activity is required for the toxic effects of mutant LRRK2ldardarin." Neurobiol. Dis. 23, 329-341. These observations suggest that over-activation of LRRK2 predisposes humans to develop some forms of Parkinson's disease.

As discussed in "Chromosomal amplification of leucine-rich repeat kinase-2 (LRRK2) is required for oncogenic MET signaling in papillary renal and thyroid carcinomas", Looyeng et al., Proceedings of the National Academy of Sciences of the United States of America (2011), 108(4), 1439-1444, S1439/1-S1439/10; language: English; database: CAPLUS, DOI:10.1073/pnas.1012500108; the receptor tyrosine kinase MET is frequently amplified in human tumors, resulting in high cell surface densities and constitutive activation even in the absence of growth factor stimulation by its endogenous ligand, hepatocyte growth factor (HGF). LRRK2 was identified and shown to be amplified and overexpressed in papillary renal and thyroid carcinomas. Down-regulation of LRRK2 in cultured tumor cells compromises MET activation and selectively reduces downstream MET signaling to mTOR and STAT3. Loss of these critical mitogenic pathways induces cell cycle arrest and cell death due to loss of ATP production, indicating that MET and LRRK2 cooperate to promote efficient tumor cell growth and survival in these cancers.

Missense mutations in LRRK2, as discussed above cause late-onset Parkinson's disease (PD). In addition, common genetic variation in LRRK2 modifies susceptibility to Crohn's disease and leprosy. See "LRRK2 inhibition attenuates microglial inflammatory responses", Moehle et al., Journal of Neuroscience (2012), 32(5), 1602-1611. Language: English, Database: CAPLUS, DOI:10.1523/JNEUROSCI.5601-11.2012.

Included among the genes identified as being associated with leprosy susceptibility or resistance, PARK2 and LRRK2 have been discussed as participating in the regulation of hostcell apoptosis. See "Leprosy susceptibility: genetic variations regulate innate and adaptive immunity, and disease outcome," Cardoso et al., Future Microbiology (2011), 6(5), 533-549. Cardoso et al. further report that the same genes associated with leprosy are also associated with autoimmune (Crohn's disease, rheumatoid arthritis, psoriasis) or neurodegenerative diseases (Parkinson's and Alzheimer's).

SUMMARY OF THE DISCLOSURE

Certain triazolopyridazine compounds have been discovered according to the present disclosure that inhibit LRRK2, and therefore find utility in the treatment of a number of disorders neurodegenerative diseases such as Parkinson's disease; precancerous conditions and cancer; autoimmune disorders such as Crohn's disease, rheumatoid arthritis and psoriasis; and leprosy.

The present disclosure is concerned with compounds represented by formula I:

I

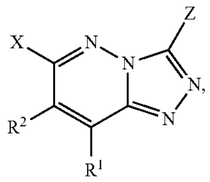

wherein

Z is a 5- or 6-membered substituted or unsubstituted aryl or substituted or unsubstituted heterocyclic ring, each of $R^1$ and $R^2$ is individually selected from the group consisting of hydrogen, halogen, an alkyl group, a substituted or unsubstituted aryl group containing 5 or 6 carbon atoms in the aryl ring;

X is selected from

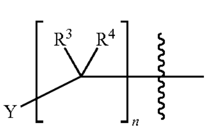

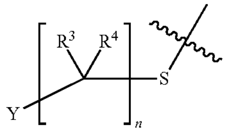

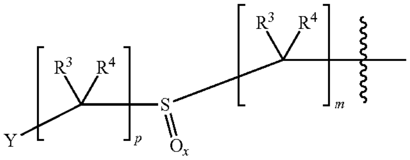

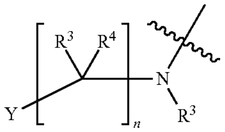

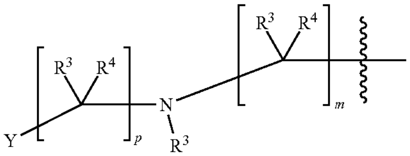

-continued

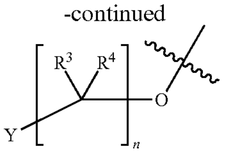

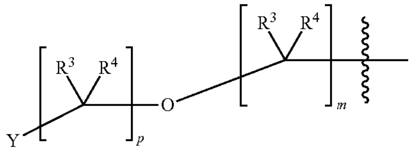

each of $R^3$ and $R^4$ is individually selected from the group consisting of hydrogen, an alkyl group; or $R^3$ and $R^4$ may be combined to form a ring moiety; or $R^3$ and $R^4$ may be combined to form a carbonyl to give a ketone, ester or amide; or either $R^3$ or $R^4$ may be —OH, —O—$R^6$ or —$NH_2$, —$NHR^6$, —$NR^6R^7$, —S—$R^6$ with the proviso that an $R^3$ or $R^4$ does not place two groups selected from —OH, —O—$R^6$ or —$NH_2$, —$NHR^6$, —$NR^6R^7$, —S—$R^6$ on the same C atom; or $R^3$ and $R^4$ may be taken together to form a double or triple bond with the proviso that they are not substituted with a $S(O)_x$, —$NH_2$, —$NH(R^6)$, —$N(R^6R^7)$—, —OH or —O—$R^6$ to give an enol, enolether, vinyl sulfone, vinylthioether, vinylsulfoxide, enamine or the like;

Y may be absent, may be hydrogen, may be substituted or unsubstituted aryl or substituted or unsubstituted heterocyclo group containing 4 to 7 atoms in the ring, or may be $COR^5$ or $S(O)_xR^5$; and $R^5$ is $NH_2$, $NHR^6$, $NR^6R^7$, substituted or unsubstituted aryl or substituted or unsubstituted heterocyclo group containing 4 to 7 atoms in the ring;

m is 1 or 2 n is 1 to 5 p is 0 to 3 x is 0, 1 or 2 each $R^6$ and $R^7$ is individually an alkyl group, an unsubstituted 5- or 6-membered saturated hydrocarbon ring;

and derivatives thereof selected from the group consisting of pharmaceutically acceptable salts, prodrugs, deuterated forms, radio-actively labeled forms, isomers, solvates and combinations thereof.

The present disclosure also relates to a pharmaceutical composition comprising at least one of the above identified compounds or derivatives, and a pharmaceutically acceptable carrier.

A further aspect of the present disclosure is concerned with a method of treating a patient having a disease caused by or associated with abnormal LRRK2 kinase activity, which comprises administering to the patient an effective treatment amount of at least one of the above identified compounds or derivatives.

Another aspect of the present disclosure is concerned with a method for treating a patient having a neurodegenerative disease, and especially Parkinson's disease, which comprises administering to the patient an effective treatment amount of at least one of the above identified compounds or derivatives.

A still further aspect of the present disclosure is concerned with a method for treating a patient having an autoimmune disease such as Crohn's disease, rheumatoid arthritis and psoriasis, which comprises administering to the patient an effective treatment amount of at least one of the above identified compounds or derivatives.

A further aspect of the present disclosure is concerned with a method for treating a patient for a precancerous condition or cancer, which comprises administering to the patient an effective treatment amount of at least one of the above identified compounds or derivatives.

Another aspect of the present disclosure is concerned with a method for treating a patient having leprosy, which comprises administering to the patient and effective treatment amount of at least one of the above identified compounds or derivatives.

The present disclosure is also concerned with enhancing the blood brain barrier transmission of the above disclosed compounds by modifying the compounds and/or employing the compounds along with another component capable of enhancing transmission of the compound through the blood brain barrier.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BEST AND VARIOUS MODES FOR CARRYING OUT DISCLOSURE

Certain triazolopyridazine compounds have been discovered according to the present disclosure that inhibit LRRK2, and therefore find utility in a number of disorders neurodegenerative diseases such as Parkinson's disease; precancerous conditions and cancer; autoimmune disorders such as Crohn's disease, rheumatoid arthritis and psoriasis; and leprosy.

The present disclosure is concerned with compounds represented by formula I:

I

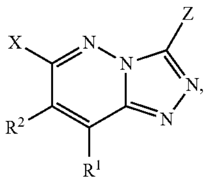

wherein

Z is a 5- or 6-membered substituted or unsubstituted aryl or substituted or unsubstituted heterocyclic ring, each of $R^1$ and $R^2$ is individually selected from the group consisting of hydrogen, halogen, an alkyl group, a substituted or unsubstituted aryl group containing 5 or 6 carbon atoms in the aryl ring;

X is selected from

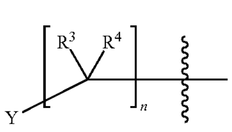

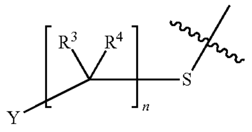

-continued

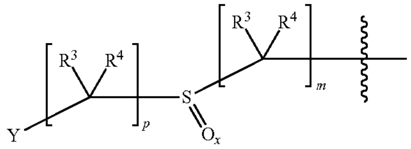

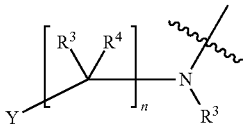

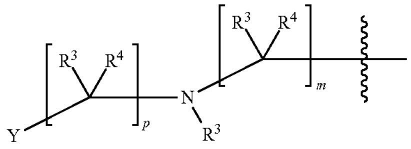

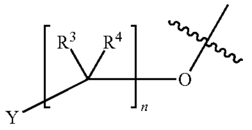

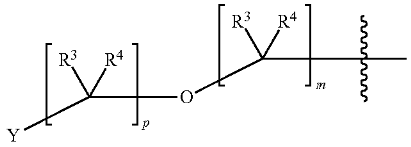

each of $R^3$ and $R^4$ is individually selected from the group consisting of hydrogen, an alkyl group; or $R^3$ and $R^4$ may be combined to form a ring moiety; or $R^3$ and $R^4$ may be combined to form a carbonyl to give a ketone, ester or amide; or either $R^3$ or $R^4$ may be —OH, —O—$R^6$ or —$NH_2$, —$NHR^6$, —$NR^6R^7$, —S—$R^6$ with the proviso that an $R^3$ or $R^4$ does not place two groups selected from —OH, —O—$R^6$ or —$NH_2$, —$NHR^6$, —$NR^6R^7$, —S—$R^6$ on the same C atom; or $R^3$ and $R^4$ may be taken together to form a double or triple bond with the proviso that they are not substituted with a $S(O)_x$, —$NH_2$, —$NH(R^6)$, —$N(R^6R^7)$—, —OH or —O—$R^6$ to give an enol, enolether, vinyl sulfone, vinylthioether, vinylsulfoxide, enamine or the like;

Y may be absent, may be hydrogen, may be substituted or unsubstituted aryl or substituted or unsubstituted heterocyclo group containing 4 to 7 atoms in the ring, or may be $COR^5$ or $S(O)_xR^5$; and $R^5$ is $NH_2$, $NHR^6$, $NR^6R^7$, substituted or unsubstituted aryl or substituted or unsubstituted heterocyclo group containing 4 to 7 atoms in the ring;

m is 1 or 2 n is 1 to 5 p is 0 to 3 x is 0, 1 or 2 each $R^6$ and $R^7$ is individually an alkyl group, an unsubstituted 5- or 6-membered saturated hydrocarbon ring;

and derivatives thereof selected from the group consisting of pharmaceutically acceptable salts, prodrugs, deuterated forms, radio-actively labeled forms, isomers, solvates and combinations thereof.

In a further embodiment, compounds of the present disclosure are represented by formula II:

II

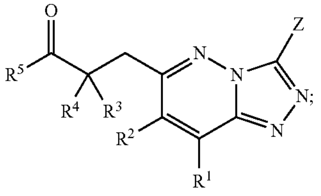

wherein $R^1$ to $R^5$ and Z are as defined above for formula I, and derivatives thereof selected from the group of pharmaceutically acceptable salts, prodrugs, deuterated forms, radio-actively labeled forms, isomers, solvates and combinations thereof.

In a particular embodiment, compounds of the present disclosure are selected from the group consisting of:

1-(piperidin-1-yl)-2-((3-(thiophen-2-yl)-[1,2,4]triazolo[4,3-b]pyridazin-6-yl)thio)butan-1-one, 2-((3-(thiophen-2-yl)-[1,2,4]triazolo[4,3-b]pyridazin-6-yl)thio)propanoic acid, 1-(piperidin-1-yl)-2-((3-(thiophen-2-yl)-[1,2,4]triazolo[4,3-b]pyridazin-6-yl)thio)propan-1-one, 1-(azetidin-1-yl)-2-((3-(thiophen-2-yl)-[1,2,4]triazolo[4,3-b]pyridazin-6-yl)thio)propan-1-one, 1-(pyrrolidin-1-yl)-2-((3-(thiophen-2-yl)-[1,2,4]triazolo[4,3-b]pyridazin-6-yl)thio)propan-1-one, 2-(methyl((3-(thiophen-2-yl)-[1,2,4]triazolo[4,3-b]pyridazin-6-yl)methyl)amino)-1-(piperidin-1-yl)propan-1-one, and derivatives thereof.

An example of an aryl ring is phenyl. The heterocyclic rings can include one or two or three heteroatoms such as N, S or O and can be heteroaryl rings. Examples of 5- and 6-membered N-heterocyclic groups are pyridyl, pyrrolidinyl, piperidinyl, piperazinyl, pyridinyl, pyrrolyl, pyrazolyl, pyrazinyl pyrimidinyl, pyridazinyl, imidazoyl, imidazolidinyl, 1,2,3-triazole and 1,2,4-triazole. Examples of O-heterocyclic groups are furanyl and pyranyl. Examples of S-heterocyclic groups are thiopyranyl and thienyl. Examples of heterocyclic groups containing both N and O are morpholinyl, oxazole, and isooxazole. Example of heterocyclic groups containing both N and S are thiomorpholine, thiazole and isothiazole. Examples of heterocyclic groups containing 4 to 7 atoms in the ring for $R^5$ are represented by the following formulae:

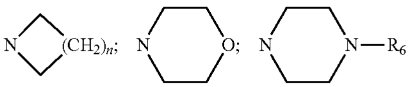

or

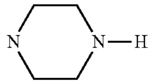

wherein n is a whole number integer from 1 to 3 and more typically 2 or 3 and may be optionally substituted or unsubstituted.

The alkyl group typically contains 1-12 carbon atoms. The alkyl group more typically contains 1-4 carbon atoms. Examples of suitable alkyl groups include methyl, ethyl and propyl. Examples branched alkyl groups include isopropyl and t-butyl.

Examples of halogen groups are F, Cl, Br and I. An example of a haloalkyl group is trifluoromethyl.

Examples of unsubstituted 5- or 6-member saturuated hydrocarbon ring are cyclopentyl and cyclohexyl.

When any of the above groups is substituted, the substitutions include at least one alkyl group, halogen group, haloalkyl, hydroxyl, alkoxy group containing 1-12 carbon atoms and more typically 1-4 carbon atoms, amino group or aminoalkyl group.

When $R^3$ and $R^4$ are combined to form a ring moiety, the ring member typically contains 3-6 atoms in the ring and can be saturated or unsaturated hydrocarbon ring or a heterocyclo ring containing at least on hetero atom selected from the group consisting of O, S and N. When $R^3$ and $R^4$ are taken together to form a double or triple bond, such is typically substituted with alkyl or unsubstituted.

The compounds according to this disclosure may form prodrugs at hydroxyl or amino functionalities using alkoxy, amino acids, etc. groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radio-actively labeled forms, isomers, solvates and combinations thereof. The "combinations" mentioned in this context are refer to derivatives falling within at least two of the groups: pharmaceutically acceptable salts, prodrugs, deuterated forms, radio-actively labeled forms, isomers, and solvates.

"Pharmaceutically acceptable salts" refer to derivatives of the disclosed compounds wherein the parent compound is modified by making acid or base salts thereof. The compounds of this disclosure form acid addition salts with a wide variety of organic and inorganic acids and include the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric acid, and the like. Salts derived from organic acids, such as aliphatic mono- and dicarboxylic acids, phenyl substituted alkanoic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

It is understood that the compounds of the present disclosure relate to all optical isomers and stereo-isomers at the various possible atoms of the molecule, unless specified otherwise. Compounds may be separated or prepared as their pure enantiomers or diasteriomers by crystallization, chromatography or synthesis.

The deuterated forms contain heavy hydrogen including deuterium. The carbon labeled forms may contain carbon-13.

Examples of radio-actively labeled forms include compounds labeled with tritium, phosphorous-32, iodine-129, carbon-11, fluorine-18, and the like.

"Solvates" refers to the compound formed by the interaction of a solvent and a solute and includes hydrates. Solvates are usually crystalline solid adducts containing solvent molecules within the crystal structure, in either stoichiometric or nonstoichiometric proportions.

The term "comprising" (and its grammatical variations) as used herein is used in the inclusive sense of "having" or "including" and not in the exclusive sense of "consisting of." The terms "a" and "the" as used herein are understood to encompass the plural as well as the singular.

Examples of compounds according to the present disclosure are shown in the table below:

| Example # | Compound Names |
|---|---|
| 1 | ethyl 2-((3-(4-fluorophenyl)-[1,2,4]triazolo[4,3-b]pyridazin-6-yl)thio)butanoate |
| 2 | ethyl 2-((3-(pyridin-4-yl)-[1,2,4]triazolo[4,3-b]pyridazin-6-yl)thio)acetate |
| 3 | 2-((3-(thiophen-2-yl)-[1,2,4]triazolo[4,3-b]pyridazin-6-yl)thio)acetamide |
| 4 | 2-((3-(pyridin-4-yl)-[1,2,4]triazolo[4,3-b]pyridazin-6-yl)thio)acetamide |
| 5 | 2-((3-(thiophen-3-yl)-[1,2,4]triazolo[4,3-b]pyridazin-6-yl)thio)acetamide |
| 6 | 2-((3-(4-fluorophenyl)-[1,2,4]triazolo[4,3-b]pyridazin-6-yl)thio)butanoic acid |
| 7 | 2-((3-(4-fluorophenyl)-[1,2,4]triazolo[4,3-b]pyridazin-6-yl)thio)-N-(thiazol-2-yl)butanamide |
| 8 | 2-((3-(4-fluorophenyl)-[1,2,4]triazolo[4,3-b]pyridazin-6-yl)thio)-1-(pyrrolidin-1-yl)butan-1-one |
| 9 | 2-((3-(4-fluorophenyl)-[1,2,4]triazolo[4,3-b]pyridazin-6-yl)thio)-1-(piperidin-1-yl)butan-1-one |
| 10 | 2-((3-cyclohexyl-[1,2,4]triazolo[4,3-b]pyridazin-6-yl)thio)acetamide |
| 11 | 1-(piperidin-1-yl)-2-((3-(thiophen-2-yl)-[1,2,4]triazolo[4,3-b]pyridazin-6-yl)thio)ethanone |
| 12 | 2-((3-(4-fluorophenyl)-[1,2,4]triazolo[4,3-b]pyridazin-6-yl)thio)-N-(quinolin-2-yl)butanamide |
| 13 | 2-((3-(p-tolyl)-[1,2,4]triazolo[4,3-b]pyridazin-6-yl)thio)acetic acid |
| 14 | 2-((3-(4-fluorophenyl)-[1,2,4]triazolo[4,3-b]pyridazin-6-yl)thio)-N-(2-(trifluoromethyl)phenyl)butanamide |
| 15 | 2-((3-cyclopentyl-[1,2,4]triazolo[4,3-b]pyridazin-6-yl)thio)acetamide |
| 16 | 2-((3-(pyridin-2-yl)-[1,2,4]triazolo[4,3-b]pyridazin-6-yl)thio)acetamide |
| 17 | 2-((3-(4-fluorophenyl)-[1,2,4]triazolo[4,3-b]pyridazin-6-yl)thio)acetic acid |
| 18 | 2-((3-(thiophen-2-yl)-[1,2,4]triazolo[4,3-b]pyridazin-6-yl)thio)butanoic acid |
| 19 | 2-((3-(4-fluorophenyl)-[1,2,4]triazolo[4,3-b]pyridazin-6-yl)thio)acetamide |
| 20 | 6-(piperidin-1-yl)-3-(thiophen-2-yl)-[1,2,4]triazolo[4,3-b]pyridazine |
| 21 | 1-(pyrrolidin-1-yl)-2-((3-(thiophen-2-yl)-[1,2,4]triazolo[4,3-b]pyridazin-6-yl)thio)ethanone |
| 22 | 2-((3-(thiophen-2-yl)-[1,2,4]triazolo[4,3-b]pyridazin-6-yl)thio)-N-(p-tolyl)acetamide |
| 23 | N-(thiazol-2-yl)-2-((3-(thiophen-2-yl)-[1,2,4]triazolo[4,3-b]pyridazin-6-yl)thio)acetamide |
| 24 | 1-morpholino-2-((3-(thiophen-2-yl)-[1,2,4]triazolo[4,3-b]pyridazin-6-yl)thio)ethanone |
| 25 | 1-(pyrrolidin-1-yl)-2-((3-(p-tolyl)-[1,2,4]triazolo[4,3-b]pyridazin-6-yl)thio)ethanone |
| 26 | 2-((3-(furan-2-yl)-[1,2,4]triazolo[4,3-b]pyridazin-6-yl)thio)acetamide |
| 27 | 2-((3-(thiophen-2-yl)-[1,2,4]triazolo[4,3-b]pyridazin-6-yl)thio)acetic acid |
| 28 | 2-((3-(furan-2-yl)-[1,2,4]triazolo[4,3-b]pyridazin-6-yl)thio)acetic acid |
| 29 | 2-((3-(benzo[b]thiophen-2-yl)-[1,2,4]triazolo[4,3-b]pyridazin-6-yl)thio)acetamide |
| 30 | 2-((3-(benzo[b]thiophen-2-yl)-[1,2,4]triazolo[4,3-b]pyridazin-6-yl)thio)acetic acid |
| 31 | 2-((3-(benzofuran-2-yl)-[1,2,4]triazolo[4,3-b]pyridazin-6-yl)thio)acetic acid |
| 32 | 2-((3-(benzofuran-2-yl)-[1,2,4]triazolo[4,3-b]pyridazin-6-yl)thio)acetamide |
| 33 | 2-((3-(thiazol-2-yl)-[1,2,4]triazolo[4,3-b]pyridazin-6-yl)thio)butanoic acid |
| 34 | 1-(piperidin-1-yl)-2-((3-(thiophen-2-yl)-[1,2,4]triazolo[4,3-b]pyridazin-6-yl)thio)butan-1-one |
| 35 | 2-((3-(benzo[b]thiophen-3-yl)-[1,2,4]triazolo[4,3-b]pyridazin-6-yl)thio)acetamide |
| 36 | 2-((3-(thiophen-2-yl)-[1,2,4]triazolo[4,3-b]pyridazin-6-yl)thio)propanoic acid |
| 37 | 2-((3-(thiazol-2-yl)-[1,2,4]triazolo[4,3-b]pyridazin-6-yl)thio)acetamide |
| 38 | 2-((3-(benzo[b]thiophen-3-yl)-[1,2,4]triazolo[4,3-b]pyridazin-6-yl)thio)acetic acid |
| 39 | 2-((3-(5-methyl-4-phenylthiophen-3-yl)-[1,2,4]triazolo[4,3-b]pyridazin-6-yl)thio)acetic acid |
| 40 | 2-((3-(5-methyl-4-phenylthiophen-3-yl)-[1,2,4]triazolo[4,3-b]pyridazin-6-yl)thio)acetamide |
| 41 | 2-((3-(thiophen-2-yl)-[1,2,4]triazolo[4,3-b]pyridazin-6-yl)thio)hexanoic acid |
| 42 | 2-((3-(thiazol-2-yl)-[1,2,4]triazolo[4,3-b]pyridazin-6-yl)thio)acetic acid |
| 43 | 2-((3-(4-fluorophenyl)-[1,2,4]triazolo[4,3-b]pyridazin-6-yl)thio)-N-(thiazol-2-yl)acetamide |
| 44 | 2-((3-(thiophen-2-yl)-[1,2,4]triazolo[4,3-b]pyridazin-6-yl)thio)butanamide |
| 45 | 2-((3-(4-fluorophenyl)-[1,2,4]triazolo[4,3-b]pyridazin-6-yl)thio)butanamide |
| 46 | 1-(pyrrolidin-1-yl)-2-((3-(thiophen-2-yl)-[1,2,4]triazolo[4,3-b]pyridazin-6-yl)thio)butan-1-one |
| 47 | 1-morpholino-2-((3-(thiophen-2-yl)-[1,2,4]triazolo[4,3-b]pyridazin-6-yl)thio)butan-1-one |
| 48 | 2-((3-(thiophen-2-yl)-[1,2,4]triazolo[4,3-b]pyridazin-6-yl)thio)-N-(thiophen-2-ylmethyl)butanamide |
| 49 | 2-((3-(5-methylthiophen-2-yl)-[1,2,4]triazolo[4,3-b]pyridazin-6-yl)thio)acetamide |
| 50 | 1-(azepan-1-yl)-2-((3-(thiophen-2-yl)-[1,2,4]triazolo[4,3-b]pyridazin-6-yl)thio)butan-1-one |
| 51 | 1-(3-methylpiperidin-1-yl)-2-((3-(thiophen-2-yl)-[1,2,4]triazolo[4,3-b]pyridazin-6-yl)thio)butan-1-one |
| 52 | N-cyclohexyl-2-((3-(thiophen-2-yl)-[1,2,4]triazolo[4,3-b]pyridazin-6-yl)thio)butanamide |
| 53 | 2-((3-(4-(trifluoromethyl)phenyl)-[1,2,4]triazolo[4,3-b]pyridazin-6-yl)thio)butanoic acid |
| 54 | 2-((3-(3,4-difluorophenyl)-[1,2,4]triazolo[4,3-b]pyridazin-6-yl)thio)butanoic acid |
| 55 | 2-((3-(2-fluorophenyl)-[1,2,4]triazolo[4,3-b]pyridazin-6-yl)thio)butanoic acid |
| 56 | 2-((3-(3-fluorophenyl)-[1,2,4]triazolo[4,3-b]pyridazin-6-yl)thio)butanoic acid |

-continued

| Example # | Compound Names |
|---|---|
| 57 | 2-((3-(5-methylthiophen-2-yl)-[1,2,4]triazolo[4,3-b]pyridazin-6-yl)thio)-1-(piperidin-1-yl)ethanone |
| 58 | 1-(4-methylpiperazin-1-yl)-2-((3-(thiophen-2-yl)-[1,2,4]triazolo[4,3-b]pyridazin-6-yl)thio)butan-1-one |
| 59 | 2-((3-(5-methylthiophen-2-yl)-[1,2,4]triazolo[4,3-b]pyridazin-6-yl)thio)-1-(piperidin-1-yl)butan-1-one |
| 60 | 1-(piperidin-1-yl)-2-((3-(thiazol-2-yl)-[1,2,4]triazolo[4,3-b]pyridazin-6-yl)thio)butan-1-one |
| 61 | 2-((3-(5-chlorothiophen-2-yl)-[1,2,4]triazolo[4,3-b]pyridazin-6-yl)thio)butanoic acid |
| 62 | 2-((3-(5-chlorothiophen-2-yl)-[1,2,4]triazolo[4,3-b]pyridazin-6-yl)thio)-1-(piperidin-1-yl)butan-1-one |
| 63 | 2-((3-(5-chlorothiophen-2-yl)-[1,2,4]triazolo[4,3-b]pyridazin-6-yl)thio)-1-(pyrrolidin-1-yl)butan-1-one |
| 64 | 1-(piperidin-1-yl)-2-((3-(thiophen-3-yl)-[1,2,4]triazolo[4,3-b]pyridazin-6-yl)thio)butan-1-one |
| 65 | ethyl 2-((3-(4-methoxyphenyl)-[1,2,4]triazolo[4,3-b]pyridazin-6-yl)thio)butanoate |
| 66 | 2-((3-(4-methoxyphenyl)-[1,2,4]triazolo[4,3-b]pyridazin-6-yl)thio)butanamide |
| 67 | 2-((3-(4-methoxyphenyl)-[1,2,4]triazolo[4,3-b]pyridazin-6-yl)thio)-1-(piperidin-1-yl)butan-1-one |
| 68 | ethyl 2-((3-(2-methoxyphenyl)-[1,2,4]triazolo[4,3-b]pyridazin-6-yl)thio)butanoate |
| 69 | 2-((3-(2-methoxyphenyl)-[1,2,4]triazolo[4,3-b]pyridazin-6-yl)thio)butanamide |
| 70 | 2-((3-(2-methoxyphenyl)-[1,2,4]triazolo[4,3-b]pyridazin-6-yl)thio)-1-(piperidin-1-yl)butan-1-one |
| 71 | ethyl 2-((3-(3-methoxyphenyl)-[1,2,4]triazolo[4,3-b]pyridazin-6-yl)thio)butanoate |
| 72 | 2-((3-(3-methoxyphenyl)-[1,2,4]triazolo[4,3-b]pyridazin-6-yl)thio)butanamide |
| 73 | 2-((3-(3-methoxyphenyl)-[1,2,4]triazolo[4,3-b]pyridazin-6-yl)thio)-1-(piperidin-1-yl)butan-1-one |
| 74 | ethyl 2-((3-(2-fluorophenyl)-[1,2,4]triazolo[4,3-b]pyridazin-6-yl)thio)butanoate |
| 75 | ethyl 2-((3-(3-fluorophenyl)-[1,2,4]triazolo[4,3-b]pyridazin-6-yl)thio)butanoate |
| 76 | ethyl 2-((3-(3,4-difluorophenyl)-[1,2,4]triazolo[4,3-b]pyridazin-6-yl)thio)butanoate |
| 77 | ethyl 2-((3-(4-(trifluoromethyl)phenyl)-[1,2,4]triazolo[4,3-b]pyridazin-6-yl)thio)butanoate |
| 78 | 2-((3-(4-(trifluoromethyl)phenyl)-[1,2,4]triazolo[4,3-b]pyridazin-6-yl)thio)butanamide |
| 79 | 2-((3-(3,4-difluorophenyl)-[1,2,4]triazolo[4,3-b]pyridazin-6-yl)thio)butanamide |
| 80 | 2-((3-(2-fluorophenyl)-[1,2,4]triazolo[4,3-b]pyridazin-6-yl)thio)butanamide |
| 81 | 2-((3-(3-fluorophenyl)-[1,2,4]triazolo[4,3-b]pyridazin-6-yl)thio)butanamide |
| 82 | ethyl 2-((3-(thiophen-2-yl)-[1,2,4]triazolo[4,3-b]pyridazin-6-yl)oxy)butanoate |
| 83 | 2-((3-(thiophen-2-yl)-[1,2,4]triazolo[4,3-b]pyridazin-6-yl)oxy)butanoic acid |
| 84 | 2-((3-(thiophen-2-yl)-[1,2,4]triazolo[4,3-b]pyridazin-6-yl)oxy)butanamide |
| 85 | 1-(piperidin-1-yl)-2-((3-(thiophen-2-yl)-[1,2,4]triazolo[4,3-b]pyridazin-6-yl)oxy)butan-1-one |
| 86 | N-phenyl-2-((3-(thiophen-2-yl)-[1,2,4]triazolo[4,3-b]pyridazin-6-yl)thio)butanamide |
| 87 | 2-((3-(5-ethylthiophen-2-yl)-[1,2,4]triazolo[4,3-b]pyridazin-6-yl)thio)-1-(piperidin-1-yl)butan-1-one |
| 88 | 2-((3-(5-ethylthiophen-2-yl)imidazo[1,2-b]pyridazin-6-yl)thio)butanoic acid |
| 89 | 2-((3-(5-methylthiophen-2-yl)-[1,2,4]triazolo[4,3-b]pyridazin-6-yl)thio)butanoic acid |
| 90 | 1-(piperidin-1-yl)-2-((3-(thiophen-2-yl)-[1,2,4]triazolo[4,3-b]pyridazin-6-yl)thio)propan-1-one |
| 91 | 2-((3-(thiophen-2-yl)-[1,2,4]triazolo[4,3-b]pyridazin-6-yl)sulfonyl)acetamide |
| 92 | 2-((3-(thiophen-2-yl)-[1,2,4]triazolo[4,3-b]pyridazin-6-yl)thio)pentanoic acid |
| 93 | 1-(piperidin-1-yl)-2-((3-(thiophen-2-yl)-[1,2,4]triazolo[4,3-b]pyridazin-6-yl)thio)pentan-1-one |
| 94 | 2-((3-(2-fluorophenyl)-[1,2,4]triazolo[4,3-b]pyridazin-6-yl)thio)-1-(piperidin-1-yl)butan-1-one |
| 95 | 1-(piperidin-1-yl)-2-((3-(4-(trifluoromethyl)phenyl)-[1,2,4]triazolo[4,3-b]pyridazin-6-yl)thio)butan-1-one |
| 96 | 2-((3-(3,4-difluorophenyl)-[1,2,4]triazolo[4,3-b]pyridazin-6-yl)thio)-1-(piperidin-1-yl)butan-1-one |
| 97 | 2-((3-(3-fluorophenyl)-[1,2,4]triazolo[4,3-b]pyridazin-6-yl)thio)-1-(piperidin-1-yl)butan-1-one |
| 98 | methyl 2-((3-(thiophen-2-yl)-[1,2,4]triazolo[4,3-b]pyridazin-6-yl)amino)butanoate |
| 99 | 2-((3-(thiophen-2-yl)-[1,2,4]triazolo[4,3-b]pyridazin-6-yl)amino)butanamide |
| 100 | 1-(piperidin-1-yl)-2-((3-(thiophen-2-yl)-[1,2,4]triazolo[4,3-b]pyridazin-6-yl)amino)butan-1-one |
| 101 | 1-(azetidin-1-yl)-2-((3-(thiophen-2-yl)-[1,2,4]triazolo[4,3-b]pyridazin-6-yl)thio)propan-1-one |
| 102 | 1-(4,4-difluoropiperidin-1-yl)-2-((3-(thiophen-2-yl)-[1,2,4]triazolo[4,3-b]pyridazin-6-yl)thio)butan-1-one |
| 103 | ethyl 1-(2-((3-(thiophen-2-yl)-[1,2,4]triazolo[4,3-b]pyridazin-6-yl)thio)butanoyl)piperidine-3-carboxylate |
| 104 | 1-(2-methylpiperidin-1-yl)-2-((3-(thiophen-2-yl)-[1,2,4]triazolo[4,3-b]pyridazin-6-yl)thio)butan-1-one |
| 105 | 1-(pyrrolidin-1-yl)-2-((3-(thiophen-2-yl)-[1,2,4]triazolo[4,3-b]pyridazin-6-yl)thio)propan-1-one |
| 106 | 2-((3-phenyl-[1,2,4]triazolo[4,3-b]pyridazin-6-yl)thio)-1-(piperidin-1-yl)butan-1-one |
| 107 | 2-methyl-1-(pyrrolidin-1-yl)-2-((3-(thiophen-2-yl)-[1,2,4]triazolo[4,3-b]pyridazin-6-yl)thio)propan-1-one |
| 108 | 1-(piperidin-1-yl)-2-((3-(pyrazin-2-yl)-[1,2,4]triazolo[4,3-b]pyridazin-6-yl)thio)propan-1-one |
| 109 | 1-(piperidin-1-yl)-2-((3-(pyrimidin-2-yl)-[1,2,4]triazolo[4,3-b]pyridazin-6-yl)thio)propan-1-one |
| 110 | 1-(piperidin-1-yl)-2-((3-(thiazol-4-yl)-[1,2,4]triazolo[4,3-b]pyridazin-6-yl)thio)propan-1-one |
| 111 | 1-(pyrrolidin-1-yl)-2-((3-(thiazol-4-yl)-[1,2,4]triazolo[4,3-b]pyridazin-6-yl)thio)propan-1-one |
| 112 | 2-((3-(1-methyl-1H-pyrazol-5-yl)-[1,2,4]triazolo[4,3-b]pyridazin-6-yl)thio)-1-(piperidin-1-yl)propan-1-one |
| 113 | 2-((3-(1-methyl-1H-pyrazol-3-yl)-[1,2,4]triazolo[4,3-b]pyridazin-6-yl)thio)-1-(piperidin-1-yl)propan-1-one |

-continued

| Example # | Compound Names |
|---|---|
| 114 | 1-(azetidin-1-yl)-2-((3-(thiophen-2-yl)-[1,2,4]triazolo[4,3-b]pyridazin-6-yl)thio)butan-1-one |
| 115 | 2-((3-(1H-pyrazol-5-yl)-[1,2,4]triazolo[4,3-b]pyridazin-6-yl)thio)-1-(piperidin-1-yl)propan-1-one |
| 116 | 1-(piperidin-1-yl)-2-((3-(pyridazin-4-yl)-[1,2,4]triazolo[4,3-b]pyridazin-6-yl)thio)propan-1-one |
| 117 | N,N-diethyl-2-((3-(thiophen-2-yl)-[1,2,4]triazolo[4,3-b]pyridazin-6-yl)thio)propanamide |
| 118 | N,N-dimethyl-2-((3-(thiophen-2-yl)-[1,2,4]triazolo[4,3-b]pyridazin-6-yl)thio)propanamide |
| 119 | N-methyl-2-((3-(thiophen-2-yl)-[1,2,4]triazolo[4,3-b]pyridazin-6-yl)thio)propanamide |
| 120 | 2-((3-(1-methyl-1H-imidazol-2-yl)-[1,2,4]triazolo[4,3-b]pyridazin-6-yl)thio)-1-(piperidin-1-yl)propan-1-one |
| 121 | N,N-dimethyl-2-((3-(thiophen-2-yl)-[1,2,4]triazolo[4,3-b]pyridazin-6-yl)thio)butanamide |
| 122 | N-(2-hydroxyethyl)-2-((3-(thiophen-2-yl)-[1,2,4]triazolo[4,3-b]pyridazin-6-yl)thio)propanamide |
| 123 | N,N-dipropyl-2-((3-(thiophen-2-yl)-[1,2,4]triazolo[4,3-b]pyridazin-6-yl)thio)propanamide |
| 124 | 2-((3-(thiazol-2-yl)-[1,2,4]triazolo[4,3-b]pyridazin-6-yl)thio)propanoic acid |
| 125 | 1-(piperidin-1-yl)-2-((3-(thiazol-2-yl)-[1,2,4]triazolo[4,3-b]pyridazin-6-yl)thio)propan-1-one |
| 126 | 1-(azetidin-1-yl)-2-((3-(thiazol-2-yl)-[1,2,4]triazolo[4,3-b]pyridazin-6-yl)thio)propan-1-one |

Synthesis

Compounds according to the present disclosure can, for example, be prepared by the methods outlined below. A practitioner skilled in the art will understand the appropriate use of protecting groups [see: Greene and Wuts, *Protective Groups in Organic Synthesis*] and the preparation of known compounds found in the literature using the standard methods of organic synthesis. There may come from time to time the need to rearrange the order of the recommended synthetic steps, however this will be apparent to the judgment of a chemist skilled in the art of organic synthesis.

Compounds of formula I found in this disclosure can be prepared by a variety of methods; one example is illustrated in Scheme I for compounds where X=—C($R^3R^4$)C(O)OH, —C($R^3R^4$)C(O)O$R^5$, —C($R^3R^4$)C(O)N$R^6R^7$, —C($R^3R^4$)C(O)NH$R^6$ or —C($R^3R^4$)C(O)$NH_2$. Commercially available 3-chloro-5-thiopyridazine [or an analog with substituted $R^1$ or $R^2$] is alkylated with a 1-chloroacetic acid ester analog which may be substituted at $R^3$ and $R^4$ using a variety of bases ($Na_2CO_3$, NaOH, $Et_3N$) in solvents such as DMF, acetone, butanone, THF, EtOH and the like at a temperature range of −10° C. to reflux temperature. Transfromation of the resulting SCHEME I. Preparation of some compounds of formula I.

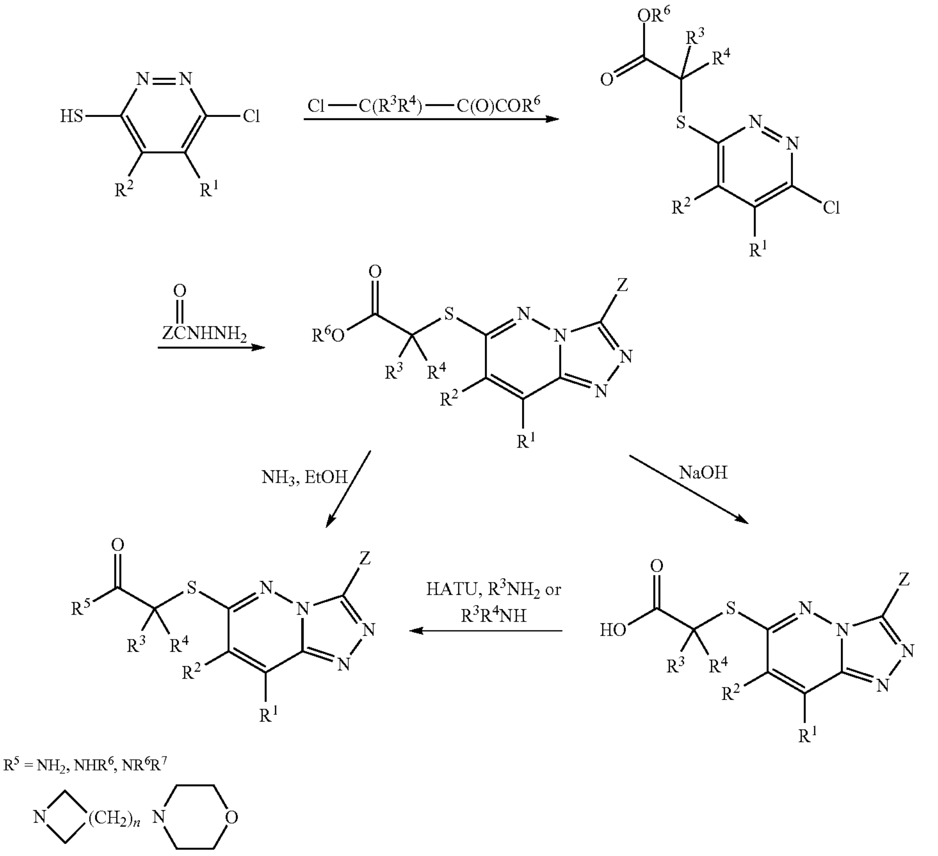

alkylation product to the triazolopyridazine can be managed by heating up to reflux temperature in an alcohol solvent such as butanol or ethanol a mixture of the chloropyridazine with an acylhydrazide substituted with the required group Z as described in formula I. This results in a concomitant N-alkylation of the chloropyridazine followed by a cyclocondensation to the triazolopyridazine product.

SCHEME II. Preparation of some compounds of formula I.

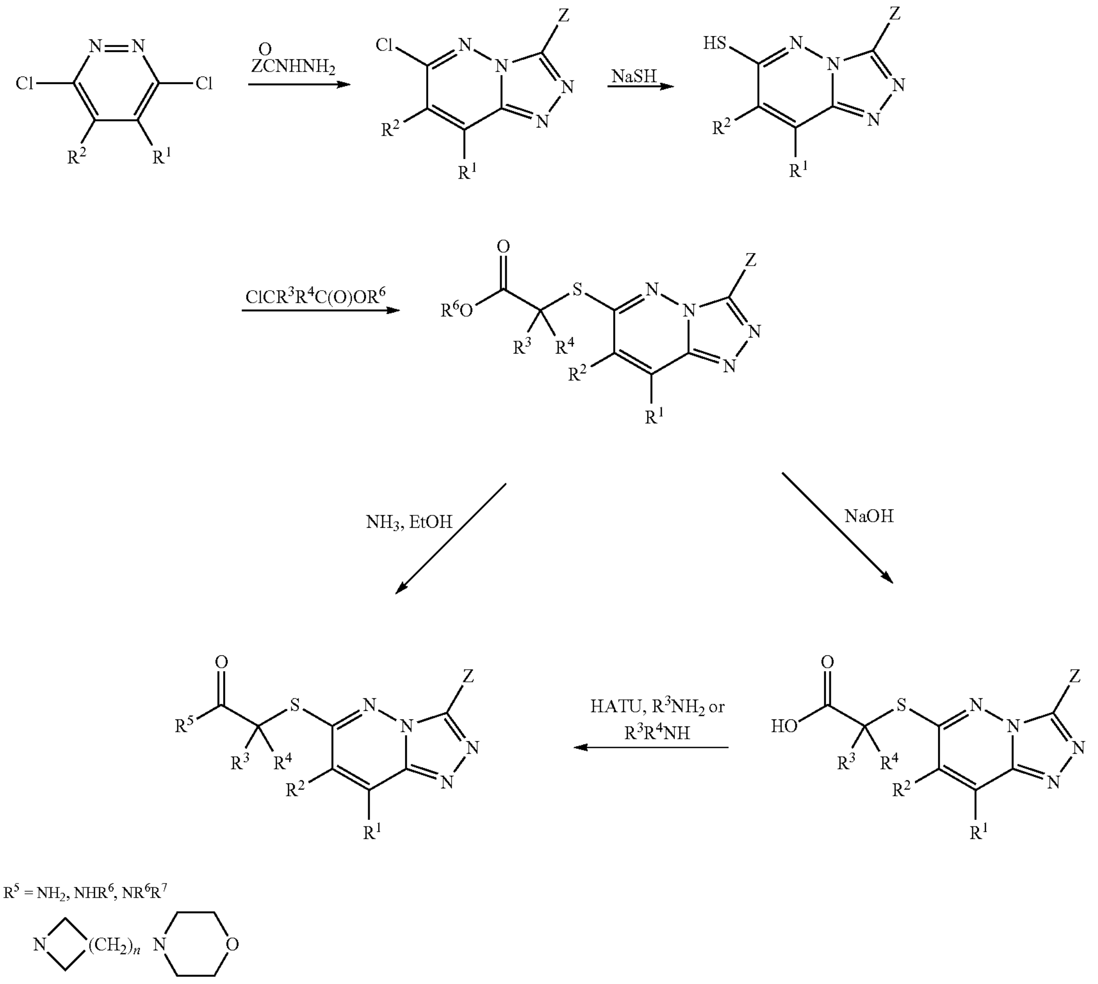

Scheme II illustrates an alternative approach where the order of the first three steps is interchanged from the order described in Scheme I. This method leads to the synthesis of the 6-chlorotriazolopyridazine which is a convenient intermediate for the preparation of a variety of analogs [Scheme III].

SCHEME III. Preparation of some compounds of formula I.

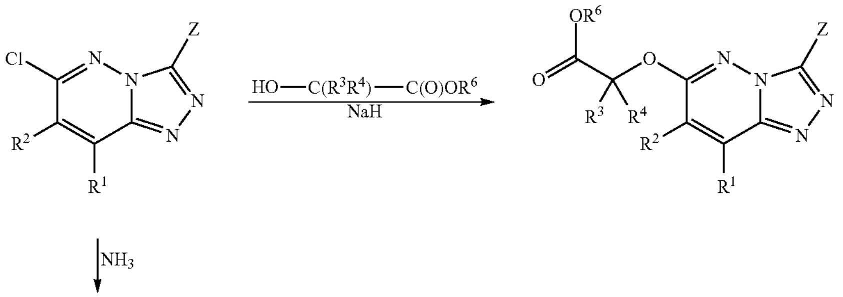

-continued

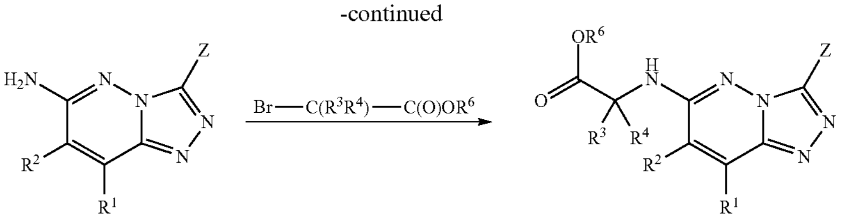

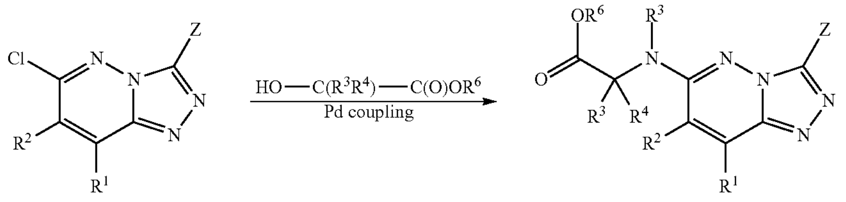

The 6-chlorotriazolopyridazine intermediate serves as a starting point for compounds where the thioether linkage is replaced by an ether linkage or an amine. The sodium salt of a hydroxyacetic acid ester analog prepared from NaH in dry DMF is stirred with cooling until the starting material is consumed. The resulting product is an —O— linked ester which can be hydrolyzed to the acid and coupled with an amine to give amides as described in Schemata I and II. Elaboration of 6-chlorotriazolopyridazine to an amine linked compound can best be realized by treating the chloro compound with neat distilled, liquid ammonia in a pressure bomb at high temperature and pressure until all of the 6-chlorotriazolopyridazine is consumed. The resulting 6-$NH_2$ analog is alkylated with an alpha-haloacetic acid ester analog to give an ester product which can be transformed to the acid and amide as described before. Finally metal coupling chemistry championed by Buchwald or by Chan and Lam would be useful for the direct transformation of the 6-chlorotriazolopyridazine to the N-linked esters with a judicious choice of conditions.

SCHEME IV. Further elaboration of the ester side chain.

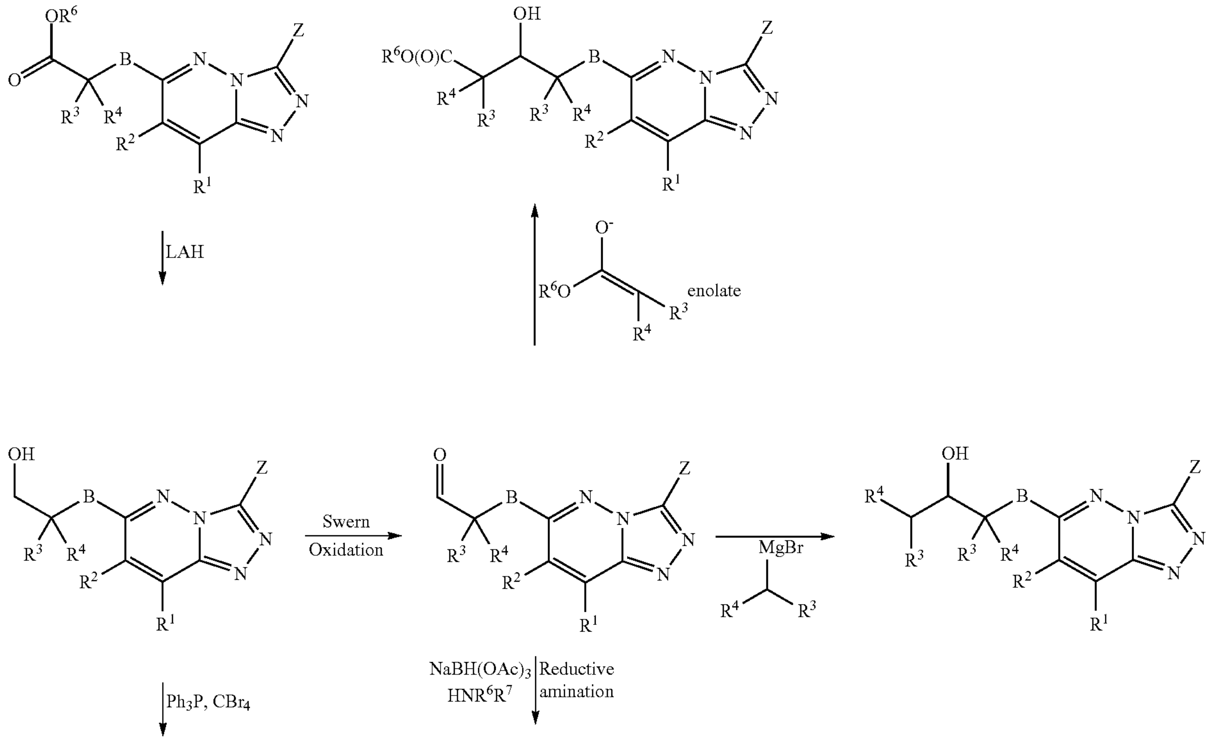

-continued

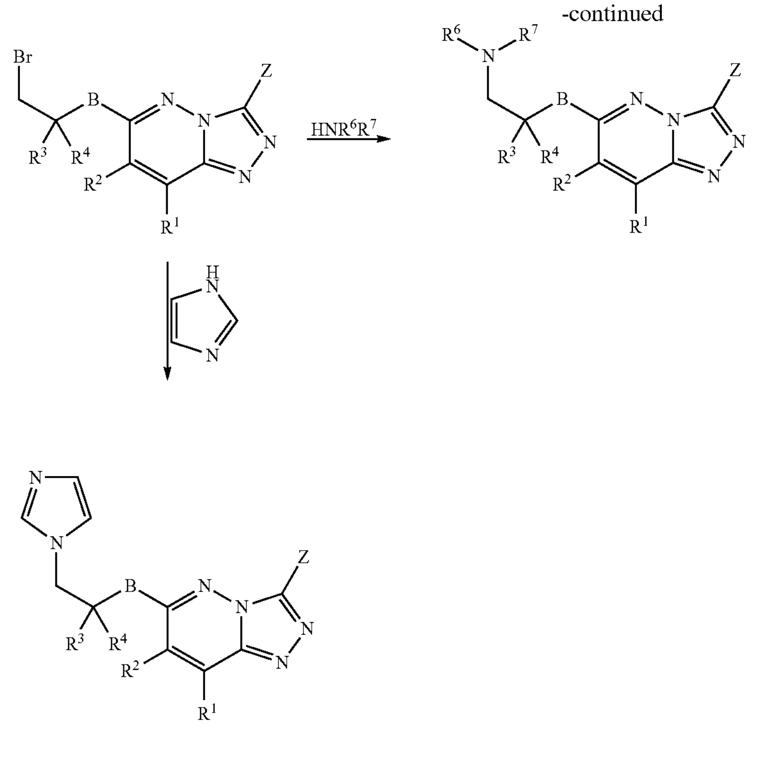

B = —S—, —O—, —NR$^3$—

The triazolopyridazine with an ester side chain linked to it by a —S—, —O—, —N($R^3$)— provides a convenient starting point for many analogs of formula I. The terminal ester can be converted to an alcohol group by a reducing agent such as lithium aluminum hydride (LAH) and the like, in an ethereal solvent such as THF, $Et_2O$ or dioxane at temperatures ranging from −78° C. to reflux temperature of the solvent. Three paths are open to the utilization of this alcohol: i) transformation into a leaving group such as a halogen ($POCl_3$ or $CCl_4/Ph_3P$ for chloro-derivatives; $PBr_3$ or $CBr_4/Ph_3P$ for bromo-derivatives etc.) or a sulfonate ester (methane sulfonyl chloride/$CH_2Cl_2/Et_3N$ or p-toluene sulfonyl chloride/pyridine) then displacement with an amine $H_2NR^6$, $HNR^6R^7$ (in a non-polar aprotic solvent such as DMF or DMSO, alternatively an alcoholic solvent such as EtOH or n-BuOH may be used, at temperatures ranging from 0° C. to reflux) or ammonia (liquid ammonia, pressure bomb with temperatures ranging from ambient to 200° C.); ii) the alcohol group is transformed into a leaving group as described above and subsequently displaced with a substituted or unsubstituted heterocycle (provided N remains unsubstituted) such as imidazole, pyrazole, triazoles, tetrazole, indole, indazole, benzimidazole in polar protic an aprotic solvents such as EtOH, n-BuOH, DMF or DMSO at temperatures ranging from 0° C. to the reflux temperature of the solvent, bases such as $Na_2CO_3$, KOH, $Et_3N$ or Hunigs base may be used as well; iii) the alcohol may be oxidized to an aldehydes with reagents such as PDC or PCC in dichloromethane or the Swern oxidation (dichloromethane, DMSO, oxalyl chloride, then $Et_3N$). A practitioner skilled in art of organic chemical synthesis will recognize that the derived aldehydes are particularly useful intermediates. They may be transformed into amines by reductive amination under a variety of conditions with an amine such as $NH_3$, $H_2NR^6$ or $HNR^6R^7$ with reagents systems such as: $H_2$(g) and Pd—C catalyst in alcohol solvent, $NaBH(OAc)_3$, $CH_2Cl_2$, $NaBH_3(CN)$ etc. A second use is for enolate condensation chemistry with an ester or ketone with strong hindered base such as lithium diisopropylamide in a solvent such as THF, $Et_2O$ or dioxane at temperatures ranging from −78° C. to ambient temperature. A third use is for addition by alkyl or aryl lithium or alkyl or aryl Grignard reagents or other metallated alkyl, aryl, heteroalkyl or heteroaryl species. Suitable solvents for these reactions include THF, $Et_2O$ or dioxane; reaction temperatures range from −78° C. to reflux temperature of the solvent.

Scheme V. C-linked compounds of formula I.

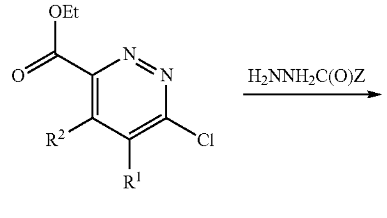

-continued

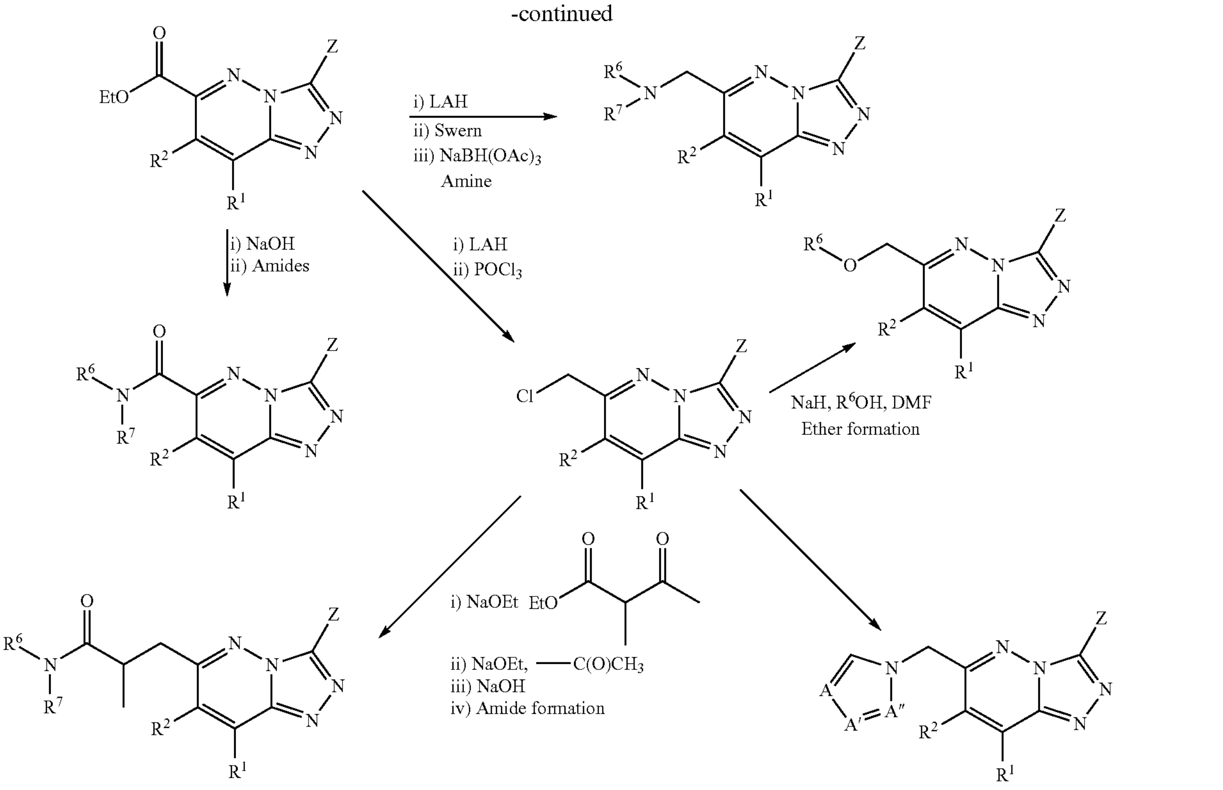

The commercially available ethyl 3-carboxyl-5-chloropyridazine is reacted with the appropriate acylhydrazide under conditions similar to those described previously. The resulting ethyl 6-carboxyltriazolopyridazine can be transformed to an amide by first hydrolysis of the ester functionality under basic or acidic conditions, then using methods described above, transformed to the amide with a peptide coupling reagent, a trialkyl amine base, in DMF with an appropriate amine. Reduction of the ester and oxidation of the resulting alcohol gives an aldehyde that can undergo reductive amination with an appropriate amine under the conditions described previously. The further utility of aldehydes of this type is described further in Scheme IV.

Transformation of the alcohol resulting from reduction of the ester to a primary halo-compound gives an alkylating that can be used to prepare amine analogs or heteroaryl analogs and also homolgate the side chain by alkylation with a 2-alkyl acetoacetate ester with NaOEt in EtOH. The acetyl group is removed by a retroaldol in refluxing NaOEt in EtOH. The resulting acid is ready for amide formation using any of the conditions discussed previously. The primary halo-compound is also a useful intermediate for the formation of ethers using Williamson ether synthesis conditions.

SCHEME VI. Methods for the homologation of C-linked analogs of formula I.

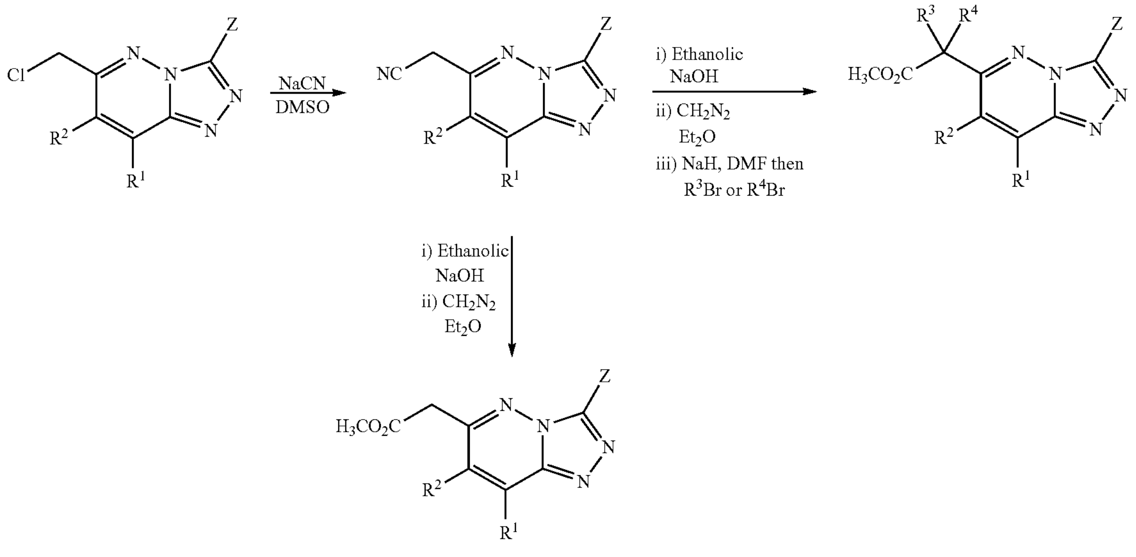

Scheme VI describes methodology for the homologation of the C-linked side chain by treating the primary halo-compound prepared in Scheme V with excess NaCN in DMSO or DMF at temperatures ranging from ambient to 60° C. The resulting cyano compound is hydrolyzed to the acid with hot ethanolic NaOH, then treated with ethereal diazomethane to give a methyl ester. This ester can then be alkylated with appropriate alkyl halides to give subsitutent $R^3$ or $R^4$ as desired. The chemist also has the option of not alkylating the ester as illustrated. In both cases the resulting esters may be transformed to various compounds of formula I using the chemistry illustrated in Schemata I through V.

It is also contemplated that from time to time a set of enantiomers or diasteromers may be produced by the action of generating a chiral center(s) during synthesis. These compounds may be separated by means of chromatography, flash chromatography, HPLC or the like, with chiral columns in the case of enantiomers and sometimes diastereomers, or separated by means of crystallization or prepared enantiomerically pure by the judicious selection of synthetic methods. All of these processes are known to persons skilled in the art of organic synthesis and need not be described herein.

EXPERIMENTAL

Preparation of ethyl 2-((6-chloropyridazin-3-yl)thio)propanoate

The synthesis of ethyl 2-((6-chloropyridazin-3-yl)thio) propanoate starts with commercially available 2-chloro-6-thiopyridazine which was added to an aqueous basic solution such as NaOH solution and the mixture was stirred for approximately 10-30 min before a solution of ethyl chloroacetate (837 mg, 7.35 mmol) in a polar solvent such as acetone was added dropwise over 10-30 min. Stirring was continued for 1-2 h, and then the reaction was allowed to stand at room temperature. The resulting solid was collected by filtration, washed with water, and then dried to give ethyl 2-((6-chloropyridazin-3-yl)thio)propanoate.

Example 2

Ethyl 2-((3-(thiophen-2-yl)-[1,2,4]triazolo[4,3-b] pyridazin-6-yl)thio)acetate To 2-thiophenecarbohydrazide (215 mg, 1.5 mmol) dissolved in n-BuOH (3 mL) was added ethyl 2-((6-chloropyridazin-3-yl)thio)propanoate (232 mg, 1 mmol), and the whole was heated for 5 h in a 140-145° C. oil bath. The reaction mixture was then cooled to room temperature (~25° C.), and the solid residue removed by filtration. The filtrate was then diluted with methylene chloride (50 mL), and washed with saturated with $NaHCO_3$ (~15 mL). The combined aqueous layers were washed twice with methylene chloride, and the organic layers were then combined, washed with brine, dried over $MgSO_4$, filtered, and evaporated. The resulting solid was then recrystallized from EtOH to give ethyl 2-((3-(thiophen-2-yl)-[1,2,4]triazolo[4,3-b]pyridazin-6-yl)thio)acetate.

The following compounds are prepared by an adaptation of this method:

| Example | MS | NMR |
|---|---|---|
| 1 | calculated for $C_{17}H_{17}FN_4O_2S{\bullet}H$ was 361.1129 found 361.1129 | 8.36-8.42 (m, 2H, Ph), 8.31 (d, 1H, pyridazine, J = 9.8 Hz), 7.42-7.48 (m, 2H, Ph), 7.39 (d, 1H, pyridazine, J = 9.8 Hz), 4.53 (t, 1H, SCH, J = 6.8 Hz), 4.08-4.16 (dq, 1H, OCH2, J = 7.1 Hz and 11.0 Hz), 3.95-4.04 (d q, 2H, $OCH_2$, J = 7.0 Hz and 10.9 Hz), 1.98-2.09 (m, 2H, $CH_2$), 1.06 (t, 3H, $CH_3$, J = 7.0 Hz), 1.04 (t, 3H, $CH_3$, J = 9.5 Hz). |
| 2 | calculated for $C_{14}H_{13}N_5O_2S{\bullet}H$ was 316.0863 found 316.0858 | 8.79-8.82 (d d, 2H, J = 1.6, 4.3 Hz), 8.38 (d, 1H, pyridazine, J = 9.8 Hz), 8.28-8.31 (d d, 2H, Ph, J = 1.5, 4.3 Hz), 7.51 (d, 1H, pyridazine, J = 9.8 Hz), 4.29 (s, 2H, $SCH_2$), 4.05 (q, 2H, $OCH_2$, J = 7.5 Hz), 1.07 (t, 3H, $CH_3$, J = 7.1 Hz). |

Example 27

2-((3-(Thiophen-2-yl)-[1,2,4]triazolo[4,3-b]pyridazin-6-yl)thio)acetic acid

To ethyl 2-((3-(thiophen-2-yl)-[1,2,4]triazolo[4,3-b]pyridazin-6-yl)thio)acetate (50 mg, 0.156 mmol) dissolved in a 2/1 mixture of THF and MeOH was added 100 uL of 2N NaOH, and the whole was stirred at room temperature for 3 h. The reaction mixture was then evaporated to dryness, the residue dissolved in water (5 mL), and the solution acidified with 6M HCl. The resulting precipitate was filtered, washed twice with cold water, and dried to give acid 2-((3-(thiophen-2-yl)-[1,2,4]triazolo[4,3-b]pyridazin-6-yl)thio)acetic acid.

The following compounds were prepared by an adaptation of this method:

| Example | MS | NMR |
|---|---|---|
| 6 | calculated for $C_{15}H_{13}FN_4O_2S{\bullet}H$ was 333.0816 found 333.0813 | 13.20 (br s, 1H, OH), 8.39-8.44 (m, 2H, Ph), 8.30 (d, 1H, pyridazine, J = 9.8 Hz), 7.40-7.46 (m, 2H, Ph), 7.37 (d, 1H, pyridazine, J = 9.8 Hz), 4.41 (t, 1H, SCH, J = 6.6 Hz), 1.98-2.09 (m, 2H, $CH_2$), 1.05 (t, 3H, $CH_3$, J = 7.2 Hz). |

-continued

| Example | MS | NMR |
|---|---|---|
| 13 | calculated for $C_{14}H_{12}N_4O_2S$•H was 301.0754 found 301.0752 | 13.04 (br s, 1H, OH), 8.28 (d, 1H, pyridazine, J = 9.8 Hz), 8.24-8.29 (mult app d), 1H, Ph, J = 8.2 Hz), 7.39 (d br d, 2H, Ph, J = 8.2 Hz), 7.39 (d, 1H, pyridazine, J = 9.4 Hz), 4.13 (s, 2H, SCH), 2.41 (s, 3H, $CH_3$). |
| 17 | calculated for $C_{15}H_9FN_4O_2S$•H was 305.0503 found 305.0499 | 13.08 (br s, 1H, OH), 8.38-8.44 (m, 2H, Ph), 8.29 (d, 1H, pyridazine, J = 9.8 Hz), 7.41 (d, 1H, pyridazine, J = 9.8 Hz), 7.37-7.43 (m, 2H, Ph), 4.12 (s, 2H, $SCH_2$). |
| 18 | calculated for $C_{13}H_{12}N_4O_2S_2$•H was 321.0474 found 321.0475 | 13.26 (br s, 1H, OH), 8.29 (d, 1H, pyridazine, J = 9.4 Hz), 8.20 (d d, 1H, thienyl, J = 1.1, 3.9 Hz), 7.87 (d d, 1H, thienyl, J = 1.1, 5.0 Hz), 7.37 (d, 1H, pyridazine, J = 9.8 Hz), 7.32 (d d, 1H, thienyl, J = 3.6, 4.7 Hz), 4.57 (t, 1H, SCH, J = 6.6 Hz), 2.04-2.24 (m, 2H, $CH_2$), 1.07 (t, 3H, $CH_3$, J = 7.5 Hz). |
| 27 | calculated for $C_{11}H_8N_4O_2S_2$•H was 293.0161 found 293.0158 | 13.09 (br s, 1H, OH), 8.29 (d, 1H, pyridazine, J = 9.8 Hz), 8.19 (d d, 1H, thienyl, J = 1.2, 3.9 Hz), 7.86 (d d, 1H, benzo, J = 1.2, 5.1 Hz), 7.41 (d, 1H, pyridazine, J = 9.4 Hz), 7.30 (d d, 1H, benzo, J = 3.5, 5.0 Hz), 4.21 (s, 2H, SCH). |
| 28 | calculated for $C_{11}H_8N_4O_3S$•H was 277.0390 found 277.0395 | 13.08 (br s, 1H, OH), 8.30 (d, 1H, pyridazine, J = 9.8 Hz), 8.00-8.04 (m, 1H, furan), 7.53 (d, 1H, furan, J = 3.5 Hz), 7.53 (d, 1H, pyridazine, J = 9.8 Hz), 6.80 (d d, 1H, furan, J = 2.0, 3.5 Hz), 4.17 (s, 2H, SCH). |
| 30 | calculated for $C_{15}H_{10}N_4O_2S_2$•H was 343.0318 found 343.0320 | 13.24 (br s, 1H, OH), 8.57 (s, 1H, thienyl), 8.33 (d, 1H, pyridazine, J = 9.7 Hz), 8.06-8.12 (m, 1H, benzo), 7.96-8.01 (m, 1H, benzo), 7.46-7.51 (m, 3H, benzo), 4.26 (s, 2H, SCH). |
| 31 | calculated for $C_{15}H_{10}N_4O_3S$•H was 327.0546 found 327.0552 | 13.24 (br s, 1H, OH), 8.36 (d, 1H, pyridazine, J = 9.4 Hz), 7.99 (s, 1H, furanyl), 7.77-7.82 (m, 2H, benzo), 7.51 (d, 1H, pyridazine, J = 9.8 Hz), 7.48 (t, 1H, benzo, J = 8.2 Hz), 7.39 (t, 1H, benzo, J = 7.7 Hz), 4.25 (s, 2H, SCH). |
| 33 | calculated for $C_{12}H_{11}N_5O_2S_2$•H was 322.0427 found 322.0423 | 13.27 (br s, 1H, OH), 8.38 (d, 1H, pyridazine, J = 9.3 Hz), 8.20 (d, 1H, thiazole, J = 3.1 Hz), 8.16 (d, 1H, thiazole, J = 3.2 Hz), 7.47 (d, 1H, pyridazine, J = 9.4 Hz), 4.71 (t, 1H, SCH, J = 6.5 Hz), 2.06-2.16 (m, 2H, $CH_2$), 1.06 (t, 3H, $CH_3$, J = 7.1 Hz). |
| 36 | calculated for $C_{12}H_{10}N_4O_2S_2$•H was 307.0318 found 307.0321 | 8.28 (d, 1H, pyridazine, J = 9.7 Hz), 8.21 (d d, 1H, thienyl, J = 1.1, 3.7 Hz), 7.86 (d d, 1H, thienyl, J = 1.2, 5.1 Hz), 7.35 (d, 1H, pyridazine, J = 9.7 Hz), 7.31 (d d, 1H, thienyl, J = 3.9, 5.1 Hz), 3.63 (q, 1H, SCH, J = 7.5 Hz), 1.68 (d, 3H, $CH_3$, J = 7.1 Hz). |
| 38 | calculated for $C_{15}H_{10}N_4O_2S_2$•H was 343.0318 found 343.0321 | 9.02-9.05 (m, 1H, benzo), 9.01 (s, 1H, thienyl), 8.35 (d, 1H, pyridazine, J = 9.4 Hz), 8.15-8.18 (m, 1H, benzo), 7.59-7.62 (m, 1H, benzo), 7.51-7.56 (m, 1H, benzo), 7.47 (d, 1H, pyridazine, J = 9.4 Hz), 4.22 (s, 2H, SCH). |
| 39 | calculated for $C_{18}H_{14}N_4O_2S_2$•H was 383.0631 found 383.0632 | 8.16 (d, 1H, pyridazine, J = 9.7 Hz), 8.09 (s, 1H, thienyl), 7.28 d, 1H, pyridazine, J = 9.8 Hz), 7.06-7.42 (Ph), 3.99 (s, 2H, $SCH_2$). |
| 41 | calculated for $C_{15}H_{16}N_4O_2S_2$•H was 349.0787 found 349.0791 | 8.18 (br s, 1H, thienyl), 8.13 (d, 1H, pyridazine, J = 9.8 Hz), 7.80 (d, 1H, thienyl, J = 5.1 Hz), 7.26-7.32 (m, 1H, thienyl), 7.23 (d, 1H, pyridazine, J = 9.8 Hz), 4.46 (br s, 1H, SCH), 1.95-2.08 (m, 2H, $CH_2$), 1.46 (br s, 2H, $CH_2$), 1.10-1.38 (m, $CH_2$), 0.60-0.80 (m, $CH_3$). |
| 42 | calculated for $C_{10}H_7N_5O_2S_2$•H was 294.0114 found 294.0114 | 13.00 (br s, 1H, OH), 8.38 (d, 1H, pyridazine, J = 9.8 Hz), 8.20 (d, 1H, thiazole, J = 3.2 Hz), 8.16 (d, 1H, thiazole, J = 3.1 Hz), 7.52 (d, 1H, pyridazine, J = 9.4 Hz), 4.26 (s, 2H, $SCH_2$). |
| 61 | calculated for $C_{13}H_{11}ClN_4O_2S_2$•H was 355.0085 found 355.0090 | 8.29 (d, 1H, pyridazine, J = 9.8 Hz), 8.03 (d, 1H, thienyl, J = 3.9 Hz), 7.39 (d, 1H, pyridazine, J = 9.8 Hz), 7.35 (d, 1H, thienyl, J = 4.3 Hz), 4.52 (t, 1H, SCH, J = 6.7 Hz), 2.06 (quint, 2H, $CH_2$, J = 7.2 Hz), 1.07 (t, 3H, $CH_3$, J = 7.3 Hz). |
| 88 | calculated for $C_{13}H_{11}ClN_4O_2S_2$•H was 349.0787 found 349.0793 | 8.26 (d, 1H, pyridazine, J = 9.7 Hz), 8.02 (d, 1H, thienyl, J = 3.5 Hz), 7.34 (d, 1H, pyridazine, J = 9.4 Hz), 7.04 (d, 1H, thienyl, J = 3.9 Hz), 4.53 (t, 1H, SCH, J = 6.7 Hz), 2.92 (q, 2H, $CH_2$, J = 7.6 Hz), 2.07 (quint, 2H, $CH_2$, J = 7.2 Hz), 1.32 (t, 3H, $CH_3$, J = 7.4 Hz), 1.08 (t, 3H, $CH_3$, J = 7.3 Hz). |
| 89 | calculated for $C_{14}H_{14}N_4O_2S_2$•H was 335.0631 found 335.0687 | 8.26 (d, 1H, pyridazine, J = 9.3 Hz), 8.00 (d, 1H, thienyl, J = 3.5 Hz), 7.34 (d, 1H, pyridazine, J = 9.4 Hz), 7.01 (d d, 1H, thienyl, J = 1.2, 3.5 Hz), 4.52 (t, 1H, SCH, J = 6.8 Hz), 2.56 (s, 3H, $CH_3$), 2.09 (quint, 2H, $CH_2$, J = 7.2 Hz), 1.07 (t, 3H, $CH_3$, J = 7.3 Hz). |
| 92 | calculated for $C_{14}H_{12}N_4O_2S_2$•H was 335.0631 found 335.0633 | 13.37 (br s, 1H, OH), 8.29 (d, 1H, pyridazine, J = 9.8 Hz), 8.21 (d d, 1H, thienyl, J = 1.1, 3.9 Hz), 7.87 (d d, 1H, thienyl, J = 1.2, 5.1 Hz), 7.37 (d, 1H, pyridazine, J = 9.7 Hz), 7.32 (d d, 1H, thienyl, J = 3.5, 5.0 Hz), 4.58 (t, 1H, SCH, J = 6.8 Hz), 1.95-2.06 (m, 2H, $CH_2$), 1.45-1.56 (m, 2H, $CH_2$), 0.93 (t, 3H, $CH_3$, J = 7.3 Hz). |

Example 3

2-((3-(Thiophen-2-yl)-[1,2,4]triazolo[4,3-b]pyridazin-6-yl)thio)acetamide

Ethanolic ammonia (5 mL) was added to intermediate ethyl 2-((3-(thiophen-2-yl)-[1,2,4]triazolo[4,3-b]pyridazin-6-yl)thio)acetate (60 mg, 0.188 mmol), the reaction vessel sealed and the mixture stirred overnight at 90-95° C. The mixture was then evaporated to dryness, the solid residue was filtered, washed 3 times with EtOH, and dried to give the desired 2-((3-(thiophen-2-yl)-[1,2,4]triazolo[4,3-b]pyridazin-6-yl)thio)acetamide.

The following compounds were prepared by an adaptation of this method:

| Example | MS | NMR |
|---|---|---|
| 6 | calculated for $C_{11}H_9N_5OS_2$•H was 292.0321 found 292.0320 | 8.26 (d, 1H, pyridazine, J = 9.8 Hz), 8.23 (d d, 1H, thienyl, J = 1.1, 3.9 Hz), 7.83 (d d, 1H, thienyl, J = 1.2, 5.1 Hz), 7.79 (br s, 1H, $NH_2$), 7.39 (d, 1H, pyridazine, J = 6.5 Hz), 7.33 (br s, 1H, $NH_2$), 7.30 (d d, 1H, thienyl, J = 3.9, 5.1 Hz), 4.07 (s, 2H, $SCH_2$). |
| 4 | calculated for $C_{12}H_{10}N_6OS$•H was 287.0710 found 287.0709 | 8.84 (d d, 2H, pyridyl, J = 1.9, 4.7 Hz), 8.36 (d d, 2H, pyridyl, J = 1.6, 4.7 Hz), 8.35 (d, 1H, pyridazine, J = 9.8 Hz), 7.80 (br s, 1H, NH), 7.47 (d, 1H, pyridazine, J = 9.8 Hz), 7.37 (br s, 1H, $NH_2$), 4.04 (s, 2H, $SCH_2$). |
| 5 | calculated for $C_{11}H_9N_5OS_2$•H was 292.0321 found 292.0320 | 8.66 (dd, 1H, thienyl, J = 1.2, 1.5 Hz), 8.26 (d, 1H, pyridazine, J = 9.4 Hz), 7.94 (d d, 1H, thienyl, J = 1.1, 5.1 Hz), 7.79 (d d, 1H, thienyl, J = 2.7, 3.0 Hz), 7.77.77-7.84 (m, 1H, $NH_2$), 7.38 (d, 1H, pyridazine, J = 9.8 Hz), 7.35 (br s, 1H, $NH_2$), 4.06 (s, 2H, $SCH_2$). |
| 10 | calculated for $C_{13}H_{17}N_5OS$•H was 292.1227 found 292.1226 | 8.12 (d, 1H, pyridazine, J = 9.4 Hz), 7.67 (br s, 1H, $NH_2$), 7.25 (d, 1H, pyridazine, J = 9.8 Hz), 7.25 (br s, 1H, $NH_2$), 3.91 (s, 2H, $SCH_2$), 3.22-3.31 (m, 1H, cyclohexyl), 1.97-2.05 (m, 2H, cyclohexyl), 1.78-1.88 (m, 2H, cyclohexyl), 1.68-1.75 (m, 2H, cyclohexyl), 1.63-1.69 (m, 2H, cyclohexyl), 1.30-1.52 (m, 2H, cyclohexyl). |
| 15 | calculated for $C_{12}H_{15}N_5OS$•H was 278.1070 found 278.1068 | 8.12 (d, 1H, pyridazine, J = 9.4 Hz), 7.68 (br s, 1H, $NH_2$), 7.25 (d, 1H, pyridazine, J = 9.7 Hz), 7.25 (br s, 1H, $NH_2$), 3.92 (s, 2H, $SCH_2$), 3.62 (quint, 1H, cyclopentyl CH, J = 8.1 Hz), 2.09-2.19 (m, 2H, cyclopentyl), 1.90-2.00 (m, 2H, cyclopentyl), 1.75-1.86 (m, 2H, cyclopentyl), 1.65-1.75 (m, 2H, cyclopentyl). |
| 16 | calculated for $C_{12}H_{10}N_6OS$•H was 287.0710 found 287.0705 | 8.78-8.82 (m, 1H, pyridyl), 8.38 (d, 1H, pyridyl, J = 7.9 Hz), 8.32 (d, 1H, pyridyl, J = 9.7 Hz), 8.07 (d t, 1H, pyridyl, J = 1.8, 7.7 Hz), 7.93 (br s, 1H, NH), 7.58-7.62 (m, 1H, pyridyl), 7.44 (d, 1H, pyridazine, J = 9.7 Hz), 7.33 (br s, 1H, $NH_2$), 3.90 (s, 2H, $SCH_2$). |
| 19 | calculated for $C_{13}H_{10}FN_5OS$•H was 304.0663 found 304.0603 | 8.42-8.49 (m, 2H, Ph), 8.27 (d, 1H, pyridazine, J = 9.8 Hz), 7.75 (br s, 1H, $NH_2$), 7.41-7.48 (m, 2H, Ph), 7.39 (d, 1H, pyridazine, J = 9.7 Hz), 7.34 (br s, 1H, $NH_2$), 4.00 (s, 2H, $SCH_2$). |
| 26 | calculated for $C_{11}H_9N_5O_2S$•H was 276.0550 found 276.0551 | 8.27 (d, 1H, pyridazine, J = 9.8 Hz), 8.01 (m, 1H, furanyl, J = 9.4 Hz), 7.77 (br s, 1H, $NH_2$), 7.58 (d d, 1H, furanyl, J = 0.8, 3.5 Hz), 7.39 (d, 1H, pyridazine, J = 9.8 Hz), 7.33 (br s, 1H, $NH_2$), 6.78 (dd, 1H, furanyl, J = 1.6, 3.5 Hz), 4.04 (s, 2H, $SCH_2$). |
| 29 | calculated for $C_{15}H_{11}N_5OS_2$•H was 342.0478 found 342.0480 | 8.61 (s, 1H, thienyl), 8.32 (d, 1H, pyridazine, J = 9.8 Hz), 8.07-8.13 (m, 2H, benzo), 7.89 (br s, 1H, $NH_2$), 7.46-7.52 (m, 2H, benzo), 7.46 (d, 1H, pyridazine, J = 9.4 Hz), 7.45 (br s, 1H, $NH_2$), 4.14 (s, 2H, $SCH_2$). |
| 32 | calculated for $C_{15}H_{11}N_5O_2S$•H was 326.0706 found 326.0711 | 8.34 (app d, 1H, pyridazine, J = 9.8 Hz), 8.05 (br s, 1H, furan), 7.89 (br s, 1H, $NH_2$), 7.84-7.87 (m, 1H, benzo), 7.48 (d, 1H, pyridazine, J = 9.7 Hz), 7.45-7.50 (m, 1H, benzo), 7.46 (br s, 1H, $NH_2$), 7.39 (app t, 1H, benzo, J = 7.5 Hz), 4.13 (s, 2H, $SCH_2$). |
| 35 | calculated for $C_{15}H_{11}N_5OS_2$•H was 342.0478 found 342.0476 | 9.09 (s, 1H, thienyl), 9.06-9.08 (m, 1H, benzo), 8.34 (d, 1H, pyridazine, J = 9.4 Hz), 8.14-8.17 (m, 1H, benzo), 7.89 (br s, 1H, $NH_2$), 7.57-7.62 (m, 1H, benzo), 7.50-7.55 (m, 1H, benzo), 7.44 (d, 1H, pyridazine, J = 9.4 Hz), 7.36 (br s, 1H, $NH_2$), 4.09 (s, 2H, $SCH_2$). |
| 37 | calculated for $C_{10}H_8N_6OS_2$•H was 293.0273 found 293.0273 | 8.37 (d, 1H, pyridazine, J = 9.7 Hz), 8.19 (d, 1H, thiazole, J = 3.5 Hz), 8.10 (d, 1H, thiazole, J = 3.1 Hz), 7.86 (br s, 1H, $NH_2$), 7.51 (d, 1H, pyridazine, J = 9.8 Hz), 7.33 (br s, 1H, $NH_2$), 4.09 (s, 2H, $SCH_2$). |
| 40 | calculated for $C_{18}H_{15}N_5OS_2$•H was 382.0791 found 382.0792 | 8.42 (s, 1H, thienyl), 8.13 (d, 1H, pyridazine, J = 9.8 Hz), 7.67 (br s, 1H, $NH_2$), 7.24-7.31 (m, 4H, Ph and $NH_2$), 7.24 (d, 1H, pyridazine, J = 9.8 Hz), 7.45 (br s, 1H, $NH_2$), 3.85 (s, 2H, $SCH_2$), 2.40 (s, 3H, $CH_3$). |
| 44 | calculated for $C_{15}H_{14}FN_5OS$•H was 332.0976 found 332.0978 | 8.42-8.46 (m, 2H, Ph), 8.27 (d, 1H, pyridazine, J = 9.8 Hz), 7.83 (br s, 1H, $NH_2$), 7.42-7.48 (m, 2H, Ph), 7.35 (br s, 1H, $NH_2$), 7.33 (d, 1H, pyridazine, J = 9.7 Hz), 4.37 (d d, 1H, SCH, J = 6.3, 7.5 Hz), 1.92-2.07 (m, 2H, $CH_2$), 1.04 (t, 3H, $CH_3$, J = 7.5 Hz). |
| 45 | calculated for $C_{13}H_{13}N_5OS_2$•H was 320.0634 found 320.0637 | 8.26 (d, 1H, pyridazine, J = 9.8 Hz), 8.22 (d d, 1H, thienyl, J = 1.1, 3.9 Hz), 7.90 (br s, 1H, $NH_2$), 7.86 (d d, 1H, thienyl, J = 1.2, 5.1 Hz), 7.36 (br s, 1H, $NH_2$), 7.32 (d, 1H, pyridazine, J = 9.4 Hz), 7.32 (d, 1H, thienyl, J = 1.2 Hz), 4.52 (d d, 1H, SCH, J = 5.5, 7.9 Hz), 1.96-2.14 (m, 2H, $CH_2$), 1.04 (t, 3H, $CH_3$, J = 7.5 Hz). |
| 49 | calculated for $C_{12}H_{11}N_5OS_2$•H was 306.0478 found 306.0486 | 8.23 (d, 1H, pyridazine, J = 9.4 Hz), 8.02 (d, 1H, thienyl, J = 3.6 Hz), 7.78 (br s, 1H, $NH_2$), 7.35 (d, 1H, pyridazine, J = 9.7 Hz), 7.32 (br s, 1H, $NH_2$), 6.98 (d d, 1H, thienyl, J = 0.8, 3.5 Hz), 4.05 (s, 2H, $SCH_2$), 2.56 (s, 3H, $CH_3$). |

Example 11

1-(Piperidin-1-yl)-2-((3-(thiophen-2-yl)-[1,2,4]triazolo[4,3-b]pyridazin-6-yl)thio)ethanone To 2-((3-(thiophen-2-yl)-[1,2,4]triazolo[4,3-b]pyridazin-6-yl)thio)acetic acid (100 mg, 0.34 mmol) dissolved in DMF (3 mL) was added HATU (150 mg), and after 15 minutes stirring, piperidine (40 mg) was added followed by DIPEA (200 μL). The mixture was stirred for room temperature overnight and then evaporated to dryness. 1-(Piperidin-1-yl)-2-((3-(thiophen-2-yl)-[1,2,4]triazolo[4,3-b]pyridazin-6-yl)thio)ethanone was then isolated by preparative TLC (silica gel plates, 9:1 $CHCl_3$/MeOH).

The following compounds are prepared by an adaptation of this method:

| Example | MS | NMR |
|---|---|---|
| 7 | calculated for $C_{18}H_{15}FN_6OS_2$•H was 415.0806 found 415.0804 | 8.31-8.36 (m, 2H, Ph), 8.28 (d, 1H, pyridazine, J = 9.8 Hz), 7.54 (d, 1H, thiazole, J = 3.9 Hz), 7.40 (d, 1H, pyridazine, J = 9.8 Hz), 7.30-7.36 (m, 2H, Ph), 7.26 (d, 1H, thiazole, J = 9.3 Hz), 4.77 (app t, 1H, SCH), 2.05-2.17 (m, 2H, $CH_2$), 1.03 (t, 3H, $CH_3$, J = 7.2 Hz). |
| 8 | calculated for $C_{19}H_{20}FN_5OS$•H was 386.1445 found 386.1448 | 8.36-8.42 (m, 2H, Ph), 8.28 (d, 1H, pyridazine, J = 9.8 Hz), 7.46-7.52 (m, 2H, Ph), 7.33 (d, 1H, pyridazine, J = 9.3 Hz), 4.75 (d d, 1H, SCH, J = 5.5, 7.8 Hz), 3.50-3.57 and 3.27-3.38 (m, 4H, $NCH_2$), 1.92-2.11 (m, 2H, $CH_2$), 1.50-1.92 (m, 4H, pyrrolidinyl), 0.97 (t, 3H, $CH_3$, J = 7.2 Hz). |
| 9 | calculated for $C_{20}H_{22}FN_5OS$•H was 400.1602 found 400.1603 | 8.35-8.40 (m, 2H, Ph), 8.29 (d, 1H, pyridazine, J = 9.8 Hz), 7.44-7.51 (m, 2H, Ph), 7.35 (d, 1H, pyridazine, J = 9.7 Hz), 5.01 (d d, 1H, SCH, J = 5.4, 7.4 Hz), 3.49-3.58 and 3.33-3.45 (m, 4H, $NCH_2$), 1.93-2.13 (m, 2H, $CH_2$), 1.50-1.66 (m, 2H, piperidyl), 1.38-1.50 (m, 4H, piperidyl), 0.96 (t, 3H, $CH_3$, J = 7.2 Hz). |
| 11 | calculated for $C_{16}H_{17}N_5OS_2$•H was 360.0947 found 360.0943 | 8.26 (d, 1H, pyridazine, J = 9.8 Hz), 8.13 (d d, 1H, thienyl, J = 0.8, 3.5 Hz), 7.89 (d d, 1H, thienyl, J = 1.2, 5.1 Hz), 7.41 (d, 1H, pyridazine, J = 9.8 Hz), 7.36 (d d, 1H, thienyl, J = 3.5, 5.1 Hz), 4.5 (s, 2H, SCH), 3.60 (br s, 2H, piperidyl $NCH_2$), 3.43-3.49 (m, 2H, piperidyl $NCH_2$), 1.64 (br s, 2H, piperidyl $CH_2$), 1.40-1.50 m, 2H, piperidyl $CH_2$), 1.24 (br s, 2H, piperidyl $CH_2$). |
| 12 | calculated for $C_{24}H_{19}FN_6OS$•H was 459.1398 found 459.1402 | 10.88 (s, 1H, NH), 8.87 (d, 1H, quinolinyl $NCH_2$), 8.63 (app d, 1H, quinolinyl, J = 2.4 Hz), 8.34-8.40 (m, 2H, Ph), 8.32 (d, 1H, pyridazine, J = 9.8 Hz), 7.96 (br d, 1H, quinolinyl, J = 7.0 Hz), 7.88-7.92 (m, 1H, quinolinyl), 7.63-7.68 (m, 1H, quinolinyl), 7.55-7.61 (m, 1H, quinolinyl), 7.42 (d, 1H, pyridazine, J = 9.8 Hz), 7.28-7.38 (m, 2H, Ph), 5.64 (br s, 1H, NH), 4.69 (t, 1H, SCH, J = 6.9 Hz), 2.19 (app quint, 2H, J = 7.3 Hz), 1.12 (t, 3H, $CH_3$, J = 7.2 Hz). |
| 14 | calculated for $C_{22}H_{17}F_4N_5OS$•H was 476.1163 found 476.1166 | 10.03 (s, 1H, NH), 8.38-8.44 (m, 2H, FPh), 8.32 (d, 1H, pyridazine, J = 9.8 Hz), 7.72 (br d, 1H, NPh, J = 7.4 Hz), 7.55 (br t, 1H, NPh), 7.40-7.47 (m, 1H, NPh), 7.40 (d, 1H, pyridazine, J = 9.8 Hz), 7.29-7.35 (app t, 2H, FPh, J = 9.0 Hz), 7.16 (br d, 1H, NPh, J = 7.8 Hz), 4.76 (t, 1H, SCH, J = 6.7 Hz), 2.13 (app quint, 2H, $CH_2$, J = 7.3 Hz), 1.11 (t, 3H, $CH_3$, J = 7.3 Hz). |
| 21 | calculated for $C_{15}H_{15}N_5OS_2$•H was 346.0791 found 346.0793 | 8.26 (d, 1H, pyridazine, J = 9.8 Hz), 8.13 (app d d, 1H, thienyl, J = 1.2, 3.9 Hz), 7.88 (d d, 1H, thienyl, J = 1.0, 4.7 Hz), 7.41 (d, 1H, pyridazine, J = 9.4 Hz), 7.32 (d d, 1H, thienyl, J = 3.5, 4.7 Hz), 4.37 (s, 2H, $SCH_2$), 3.64 (t, 2H, pyrrolidinyl $NCH_2$, J = 6.8 Hz) 3.28 (app t, 2H, pyrrolidinyl $NCH_2$, J = 7.1 Hz), 1.99 (quint, 2H, pyrrolidinyl $CH_2$, J = 6.8 Hz), 1.83 (quint, 2H, pyrrolidinyl $CH_2$, J = 6.8 Hz). |
| 22 | calculated for $C_{17}H_{12}FN_5OS_2$•H was 386.0540 found 386.0540 | 10.55 (s, 1H, NH), 8.28 (d, 1H, pyridazine, J = 9.7 Hz), 8.13 (app d d, 1H, thienyl, J = 1.2, 3.6 Hz), 7.72 (d d, 1H, thienyl, J = 1.0, 4.7 Hz), 7.60-7.65 (m, 2H, Ph), 7.43 (d, 1H, pyridazine, J = 9.8 Hz), 7.12-7.18 (app t, 2H, Ph), 7.00 (d d, 1H, thienyl, J = 3.5, 5.1 Hz), 4.33 (s, 2H, SCH). |
| 23 | calculated for $C_{14}H_{10}N_6OS_3$•H was 374.997 found 375.0150 | 12.69 (s, 1H, NH), 8.29 (d, 1H, pyridazine, J = 9.7 Hz), 8.03 (d d, 1H, thienyl, J = 1.2, 3.5 Hz), 7.67 (d d, 1H, thienyl, J = 1.1, 5.0 Hz), 7.53 (d, 1H, thiazolyl, J = 3.6 Hz), 7.45 (1H, pyridazine, J = 9.8 Hz), 7.24 (d, 1H, thiazolyl, J = 3.5 Hz), 6.96 (d d, 1H, thienyl, J = 4.6, 4.7 Hz), 4.44 (s, 2H, SCH). |
| 24 | calculated for $C_{15}H_{15}N_5O_2S_2$•H was 362.0740 found 362.0739 | 8.27 (d, 1H, pyridazine, J = 9.4 Hz), 8.14 (app d d, 1H, thienyl, J = 1.2, 3.9 Hz), 7.88-7.91 (m, 1H, thienyl), 7.42 (d, 1H, pyridazine, J = 9.8 Hz), 7.33 (d d, 1H, thienyl, J = 3.5, 4.7 Hz), 4.48 (s, 2H, SCH), 3.62-3.67 and 3.68-3.73 (m, 4H, morpholino), 3.45-3.49 and 3.56-3.60 (m, 4H, morpholino). |
| 25 | calculated for $C_{18}H_{19}N_5OS$•H was 354.1383 found 354.1288 | 8.25 (d, 1H, pyridazine, J = 9.8 Hz), 8.23 (d, 2H, Ph, J = 8.3 Hz), 7.38 (d, 1H, pyridazine, J = 9.4 Hz), 7.37 (d, 2H, Ph, J = 8.2 Hz), 4.32 (s, 2H, $SCH_2$), 3.58 (t, 2H, pyrrolidine $NCH_2$, J = 6.8 Hz), 3.29 (t, 2H, $NCH_2$, J = 7.8 Hz), 2.41 (s, 3H, CH3), 1.96 (app quint, 2H, pyrrolidine $CH_2$, J = 6.8 Hz), 1.79 (app quint, 2H, pyrrolidine $CH_2$, J = 6.8 Hz). |
| 34 | calculated for $C_{18}H_{21}N_5OS_2$•H was 388.1260 found 388.1268 | 8.28 (d, 1H, pyridazine, J = 9.8 Hz), 8.13 (d d, 1H, thienyl, J = 1.2, 4.0 Hz), 7.92 (d d, 1H, thienyl, J = 1.2, 5.1 Hz), 7.36 (app t, 1H, thienyl, J = 3.9 Hz), 7.34 (d, 1H, pyridazine, J = 9.8 Hz), 5.15-5.20 (m, 1H, SCH), 3.36-3.66 (m, 4H, piperidyl $NCH_2$), 1.96-2.17 (m, 2H, $CH_2$), 1.40-1.68 (m, 6H, piperidyl $CH_2CH_2$), 1.01 (t, 3H, $CH_3$, J = 7.2 Hz). |
| 43 | calculated for $C_{16}H_{11}FN_6OS_2$•H was 387.0493 found 387.0490 | 8.29 (d, 1H, pyridazine, J = 9.8 Hz), 8.22-8.29 (m, 2H, Ph), 7.50 (d, 1H, thienyl, J = 3.5 Hz), 7.44 (1H, pyridazine, J = 9.8 Hz), 7.12-7.20 (m, 3H), 4.33 (s, 2H, $SCH_2$). |

-continued

| Example | MS | NMR |
|---|---|---|
| 46 | calculated for $C_{17}H_{19}N_5OS_2$•H was 374.1104 found 374.1107 | 8.28 (d, 1H, pyridazine, J = 9.8 Hz), 8.14 (d d, 1H, thienyl, J = 1.2, 3.5 Hz), 7.34-7.37 (m, 1H, thienyl), 7.34 (d, 1H, pyridazine, J = 9.8 Hz), 4.92 (d d, 1H, SCH, J = 5.9, 7.9 Hz), 3.54-3.66 (m, 4H, morpholine $NCH_2$), 3.32-3.41 (m, 4H, morpholine $NCH_2$), 1.98-2.18 (m, 2H, $CH_2$), 1.75-1.95 (m, 4H, morpholine $CH_2$), 1.03 (t, 3H, $CH_3$, J = 7.4 Hz). |
| 47 | calculated for $C_{17}H_{19}N_5O_2S_2$•H was 390.1053 found 390.1052 | 8.28 (d, 1H, pyridazine, J = 9.6 Hz), 8.13 (d d, 1H, thienyl, J = 1.1, 3.6 Hz), 7.91 (d d, 1H, thienyl, J = 1.2, 5.0 Hz), 7.35 (d d, 1H, thienyl, J = 3.7, 5.0 Hz), 7.35 (d, 1H, pyridazine, J = 9.6 Hz), 5.11 (d d, 1H, SCH, J = 6.0, 7.1 Hz), 3.46-3.66 (m, 8H, morpholine $CH_2$), 1.98-2.18 (m, 2H, $CH_2$), 1.02 (t, 3H, $CH_3$, J = 7.4 Hz). |
| 48 | calculated for $C_{18}H_{17}N_5OS_3$•H was 416.0668 found 416.0669 | 9.11 (t, 1H, NH, J = 5.9 Hz), 8.26 (d, 1H, pyridazine, J = 9.7 Hz), 8.19 (d d, 1H, thienyl, J = 1.1, 3.5 Hz), 7.86 (d d, 1H, thienyl, J = 1.1, 5.0 Hz), 7.35 (d d, 1H, thienyl, J = 1.1, 5.1 Hz), 7.35 (d, 1H, pyridazine, J = 9.8 Hz), 7.30-7.34 (m, 1H, thienyl), 6.96 (d d, 1H, thienyl, J = 1.1, 3.5 Hz), 6.92 (d d, 1H, thienyl, J = 3.5, 5.1 Hz), 4.58 (d d, 1H, SCH, J = 5.4, 8.2 Hz), 4.53 (d, $CH_2$, J = 5.5 Hz), 4.43 (d d, 1H, $CH_2$, J = 5.1, 15.6 Hz), 1.99-2.50 (m, 2H, $CH_2$), 1.02 (t, 3H, $CH_3$, J = 7.4 Hz). |
| 50 | calculated for $C_{19}H_{23}N_5OS_2$•H was 402.1417 found 402.1422 | 8.28 (d, 1H, pyridazine, J = 9.8 Hz), 8.13 (d d, 1H, thienyl, J = 0.8, 3.9 Hz), 7.94 (d, 1H, thienyl, J = 4.7 Hz), 7.34-7.38 (m, 1H, thienyl), 7.33 (d, 1H, pyridazine, J = 9.8 Hz), 5.09 (d d, 1H, SCH), 3.42-3.62 (m, 4H, azepanyl $NCH_2$), 1.97-2.20 (m, 2H, $CH_2$), 1.59-1.70 and 1.43-1.56 (m, 8H, azepanyl $CH_2CH_2$), 1.02 (t, 3H, $CH_3$, J = 7.5 Hz). |
| 51 | calculated for $C_{19}H_{23}N_5OS_2$•H was 402.1417 found 402.1410 | 8.28 (d, 1H, pyridazine, J = 9.8 Hz), 8.11-8.16 (m, 1H, thienyl), 7.90-7.96 (m, 1H, thienyl), 7.32-7.38 (m, 1H, thienyl), 7.34 (d, 1H, pyridazine, J = 9.4 Hz), 5.06-5.30 (m, 1H, SCH), 4.68-4.82 (m, 1H, piperidyl NCH), 4.26-4.45 (m, 1H, piperidyl NCH), 3.78-3.90 (m, 1H, piperidyl NCH-isomer), 3.16-3.30 (m, 1H, piperidyl NCH-isomer), 2.66-2.80 (m, 1H, piperidyl NCH-isomer), 1.93-2.20 (m, 2H, $CH_2$), 1.34-1.73 (m, 6H, piperidyl $CH_2$), 1.10-1.32 (m, 3H, piperidyl $CH_3$), 0.94-1.6 (m, 3H, $CH_3$). |
| 57 | calculated for $C_{17}H_{19}N_5OS_2$•H was 374.1104 found 374.1113 | 8.24 (d, 1H, pyridazine, J = 9.7 Hz), 7.92 (d, 1H, thienyl, J = 3.5 Hz), 7.38 (d, 1H, pyridazine, J = 9.4 Hz), 7.01-7.04 (m, 1H, thienyl), 4.47 (s, 2H, SCH), 3.60 (br s, 2H, piperidinyl), 3.44-3.49 (m, 2H, piperidyl $NCH_2$), 2.57 (s, 3H, $CH_3$), 1.64 (br s, 4H piperidyl $CH_2$), 1.47 (piperidyl $CH_2$). |
| 58 | calculated for $C_{18}H_{22}N_6OS_2$•H was 403.1369 found 403.1373 | 8.28 (d, 1H, pyridazine, J = 9.8 Hz), 8.13 (d d, 1H, thiazole, J = 1.2, 3.5 Hz), 7.92 (d d, 1H, thienyl, J = 1.2, 5.1 Hz), 7.53 (app t, 1H, thienyl, J = 3.9 Hz), 7.35 (d, 1H, pyridazine, J = 9.4 Hz), 5.14 (app t, 1H, SCH, J = 6.5 Hz), 3.36-3.67 (m, 4H, piperazine $NCH_2$), 2.21-2.39 (m, 4H, piperazine $NCH_2$), 2.17 (s, 3H, $CH_3$), 1.96-2.17 (m, 2H, $CH_2$), 1.01 (t, 3H, $CH_3$, J = 7.4 Hz). |
| 59 | calculated for $C_{19}H_{23}N_5OS_2$•H was 402.1417 found 402.1423 | 8.25 (d, 1H, pyridazine, J = 9.4 Hz), 7.93 (d, 1H, thienyl, J = 3.5 Hz), 7.32 (d, 1H, pyridazine, J = 9.8 Hz), 7.14-7.17 (m, 1H, thienyl), 5.19 (t, 1H, SCH, J = 6.4 Hz), 3.40-3.64 (m, 4H, piperidyl $NCH_2$), 2.51 (s, $CH_3$), 1.92-2.18 (m, 2H, $CH_2$), 1.38-1.68 (m, 6H, piperidyl $CH_2CH_2$), 1.00 (t, 3H, $CH_3$, J = 7.5 Hz). |
| 60 | calculated for $C_{17}H_{20}N_6OS_2$•H was 389.1213 found 388.1216 | 8.37 (d, 1H, pyridazine, J = 9.7 Hz), 8.20 (d, 1H, thiazole, J = 3.1 Hz), 8.16 (d, 1H, thiazole, J = 3.1 Hz), 7.44 (d, 1H, pyridazine, J = 9.3 Hz), 5.28-5.33 (m, 1H, SCH), 3.36-3.68 (m, 4H, piperidyl $NCH_2$), 1.94-2.16 (m, 2H, $CH_2$), 1.42-1.66 (m, 6H, piperidyl $CH_2CH_2$), 0.99 (t, 3H, $CH_3$, J = 7.3 Hz). |
| 62 | calculated for $C_{18}H_{20}ClN_5OS_2$•H was 422.0871 found 422.0874 | 8.29 (d, 1H, pyridazine, J = 9.4 Hz), 8.13 (d, 1H, thienyl, J = 3.9 Hz), 7.28-7.44 (m, 1H, thienyl), 7.36 (d, 1H, pyridazine, J = 9.7 Hz), 5.17 (t, 1H, SCH, J = 6.2 Hz), 3.62-3.73 (m, 2H, piperidyl $NCH_2$), 3.30-3.56 (m, 2H, piperidyl $NCH_2$), 1.96-2.17 (m, 2H, $CH_2$), 1.37-1.70 (m, 6H, piperidyl $CH_2CH_2$), 1.01 (t, 3H, $CH_3$, J = 7.2 Hz). |
| 63 | calculated for $C_{17}H_{18}ClN_5OS_2$•H was 408.0714 found 408.0717 | 8.29 (d, 1H, pyridazine, J = 9.7 Hz), 7.97 (d, 1H, thienyl, J = 3.9 Hz), 7.40 (d, 1H, thienyl, J = 3.9 Hz), 7.36 (d, 1H, pyridazine, J = 9.4 Hz), 4.89 (d d, 1H, SCH, J = 5.9, 7.9 Hz), 3.57-3.64 (m, 2H, pyrrolidinyl $NCH_2$), 2.01-2.18 (m, 2H, $CH_2$), 1.76-1.97 (m, 4H, pyrrolidinyl $CH_2CH_2$), 1.03 (t, 3H, $CH_3$, J = 7.5 Hz). |
| 64 | calculated for $C_{18}H_{21}N_5OS_2$•H was 388.1260 found 388.1260 | 8.53 (d d, 1H, thienyl, J = 1.2, 2.7 Hz), 8.27 (d, 1H, pyridazine, J = 9.8 Hz), 7.22 (d d, 1H, thienyl, J = 1.2, 5.1 Hz), 7.85 (d d, 1H, thienyl, J = 3.1, 5.1 Hz), 7.33 (d, 1H, pyridazine, J = 9.8 Hz), 5.07 (t, 1H, SCH, J = 6.7 Hz), 3.54-3.65 and 3.30-3.50 (m, 4H, piperidyl $NCH_2$), 1.93-2.14 (m, 2H, $CH_2$), 1.36-1.67 (m, 6H, piperidyl $CH_2CH_2$), 0.99 (t, 3H, $CH_3$, J = 7.3 Hz). |
| 86 | calculated for $C_{19}H_{17}N_5OS_2$•H was 396.0947 found 396.0945 | 8.29 (d, 1H, pyridazine, J = 9.8 Hz), 8.19 (d d, 1H, thienyl, J = 1.2, 3.5 Hz), 7.92 (d d, 1H, thienyl, J = 1.3, 5.0 Hz), 7.58-7.63 (app d, 2H, phenyl, J = 7.5 Hz), 7.38 (d, 7.38 (d, 1H, pyridazine, J = 9.7 Hz), 7.28-7.38 (m, 2H, phenyl), 7.21 (d d, 1H, thienyl, J = 3.5, 5.0 Hz), 7.06-7.11 (app t, 1H, phenyl, J = 7.5 Hz), 4.73 (d d, 1H, SCH, J = 5.9, 7.4 Hz), 2.08-2.21 (m, 2H, $CH_2$), 1.10 (t, 3H, $CH_3$, J = 7.1 Hz). |
| 87 | calculated for $C_{20}H_{25}N_5OS_2$•H was 416.1573 found 416.1582 | 8.26 (d, 1H, pyridazine, J = 9.4 Hz), 7.94 (d, 1H, thienyl, J = 3.5 Hz), 7.31 (d, 1H, pyridazine, J = 9.4 Hz), 7.09 (app d, 1H, thienyl, J = 3.9 Hz), 5.20 (d d, 1H, SCH, J = 5.5, 7.0 Hz), 3.32-3.70 (m, 4H, piperidyl $NCH_2$), 2.94 (app q, 2H, $CH_2$), 1.98-2.18 (m, 2H, Et $CH_2$), 1.36-1.68 (m, 6H, piperidyl $CH_2CH_2$), 1.32 (t, 3H, $CH_3$, J = 7.4 Hz), 1.01 (t, 3H, $CH_3$, J = 7.4 Hz). |

-continued

| Example | MS | NMR |
|---|---|---|
| 90 | calculated for $C_{17}H_{19}N_5OS_2$•H was 374.1103 found 374.1113 | 8.28 (d, 1H, pyridazine, J = 9.8 Hz), 8.13 (d d, 1H, thienyl, J = 1.1, 3.5 Hz), 7.90 (d d, 1H, thienyl, J = 1.2, 5.1 Hz), 7.34-7.37 (m, 1H, thienyl), 7.34 (d, 1H, pyridazine, J = 9.4 Hz), 5.20 (d d, 1H, SCH, J = 6.6, 7.1 Hz), 3.40-3.63 (m, 4H, piperidyl $NCH_2$), 1.67 (d, 3H, $CH_3$, J = 6.6 Hz), 1.51-1.64 (m, 4H, piperidyl), 1.43-1.51 (m, 2H, piperidyl). |
| 93 | calculated for $C_{19}H_{23}N_5OS_2$•H was 402.1417 found 402.1417 | 8.28 (d, 1H, pyridazine, J = 9.8 Hz), 8.13 (d d, 1H, thienyl, J = 1.2, 3.9 Hz), 7.92 (d d, 1H, thienyl, J = 1.2, 5.1 Hz), 7.34-7.36 (m, 1H, thienyl), 7.33 (d, 1H, pyridazine, J = 9.8 Hz), 5.19 (d d, 1H, SCH, J = 6.0, 7.1 Hz), 3.35-3.66 (m, 4H, piperidyl $NCH_2$), 1.89-2.11 (m, 2H, Pr $CH_2$), 1.37-1.66 (m, 6H, piperidyl $CH_2CH_2$), 0.89 (t, 3H, $CH_3$, J = 7.2 Hz). |
| 105 | calculated for $C_{16}H_{17}N_5OS_2$•H was 360.0947 found 360.0939 | 8.28 (d, 1H, pyridazine, J = 9.8 Hz), 8.14 (d d, 1H, thienyl, J = 8.1, 3.5 Hz), 7.89 (d d, 1H, thienyl, J = 1.1, 4.7 Hz), 7.34 (d, 1H, pyridazine, J = 9.4 Hz), 7.32-7.36 (m, 1H, thienyl), 4.99 (q, 1H, SCH, J = 6.7 Hz), 3.62 (t, 2H, pyrrolidinyl $NCH_2$, J = 6.8 Hz), 3.35 (t, 2H, pyrrolidinyl $NCH_2$, J = 6.8 Hz), 1.76-1.97 (m, 4H, pyrrolidinyl $CH_2$), 1.68 (d, 3H, $CH_3$, J = 7.0 Hz). |
| 101 | calculated for $C_{19}H_{23}N_5OS_2$•H was 246.0791 found 246.0789 | 8.28 (d, 1H, pyridazine, J = 9.7 Hz), 8.16 (d d, 1H, thienyl, J = 1.1, 3.5 Hz), 7.90 (d d, 1H, thienyl, J = 1.2, 5.1 Hz), 7.34-7.38 (d d, 1H, thienyl, J = 3.9, 5.1 Hz), 7.34 (d, 1H, pyridazine, J = 9.8 Hz), 4.75 (q, 1H, SCH, J = 6.9 Hz), 4.34 (app q, 1H, azetidinyl $NCH_2$, J = 2.6 Hz), 4.27 (app q, 1H, azetidinyl $NCH_2$, J = 7.9 Hz), 3.86-3.96 (m, 2H, azetidinyl $NCH_2$), 2.17-2.29 (m, 2H, azetidinyl $CH_2$), 1.62 (d, 3H, $NCH_3$, J = 7.0 Hz). |
| 102 | calculated for $C_{18}H_{19}F_2N_5OS_2$•H was 424.1072 found 424.1080 | 8.29 (d, 1H, pyridazine, J = 9.8 Hz), 8.14 (d d, 1H, thienyl, J = 1.2, 3.6 Hz), 7.92 (d d, 1H, thienyl, J = 1.2, 5.1 Hz), 7.36 (d, 1H, pyridazine, J = 9.8 Hz), 7.35 (d d, 1H, thienyl, J = 4.0, 5.1 Hz), 5.19 (t, 1H, SCH, J = 6.5 Hz), 3.44-3.77 and 1.85-2.19 (m, 10H, piperidyl $CH_2$s, $CH_2$), 1.02 (t, 3H, $CH_3$, J = 7.2 Hz). |
| 103 | calculated for $C_{21}H_{25}N_5O_3S_2$•H was 460.1472 found 460.1462 | Complex spectrum due to the partial double bond character of the amide bond. Also, a mixture of diasteromers. 8.26-8.34 (m, 1H, pyridazine), 8.11-8.20 (m, 1H, thienyl), 7.86-7.99 (m, 1H, thienyl), 7.32-7.39 (m, 2H, pyridazine and thienyl), 5.13-5.38 (m, 1H, SCH), 3.60-4.16 (m, 5H, piperidyl $NCH_2$ and piperidyl CH), 8.16 (d, 1H, thiazole, J = 3.1 Hz), 7.44 (d, 1H, pyridazine, J = 9.3 Hz), 5.28-5.33 (m, 1H, SCH), 4.00-4.30 (m, 2H, $CH_2$), 3.00-4.00 (m, 4H, piperidyl $NCH_2$), 1.30-2.40 (m, 4 H, piperidyl $CH_2$), 1.13-1.22 (m, 3H, $CH_3$), 0.85-1.04 (m, 3H, $CH_3$). |
| 104 | calculated for $C_{19}H_{23}N_5OS_2$•H was 402.1417 found 402.1410 | 8.28 (d, 1H, pyridazine, J = 9.8 Hz), 8.11-8.16 (m, 1H, thienyl), 7.90-7.97 (m, 1H, thienyl), 7.33-7.38 (m, 1H, thienyl), 7.34 (d, 1H, pyridazine, J = 9.4 Hz), 5.06-5.30 (m, 1H, SCH), 4.68-4.82 (br s, 1H, piperidyl NCH), 4.26-4.44 (m, 3H, piperidyl $NCH_2$), 3.78-3.90 (m, 3H, piperidyl $NCH_2$), 1.92-2.19 (m, 2H, $CH_2$), 1.10-1.73 (m, 6H, piperidyl $CH_2$), 1.12 (app d, 3H, piperidyl $CH_3$, J = 7.1 H), 0.94-1.06 (m, 3H, Et $CH_3$). |
| 108 | calculated for $C_{17}H_{19}N_7OS$•H was 370.1445 found 370.1449 | 9.51 (d, 1H, piperazine, J = 1.6 Hz), 8.91 (app d, 1H, piperazine, J = 0.7 Hz), 8.85 (d, 1H, piperazine, J = 0.9 Hz), 8.36 (d, 1H, pyridazine, J = 9.7 Hz), 7.43 (d, 1H, pyridazine, J = 9.8 Hz), 5.15 (q, 1H, SCH, J = 6.8 Hz), 3.30-3.60 (m, 4H, piperidyl $NCH_2$), 1.58 (d, 3H, $CH_3$, J = 7.0 Hz), 1.40-1.64 (m, 6H, piperidinyl $CH_2$). |
| 109 | calculated for $C_{17}H_{19}N_7OS$•H was 370.1445 found 370.1446 | 9.08 (d, 1H, pyrimidine, J = 5.1 Hz), 8.34 (d, 1H, pyrimidine, J = 9.4 Hz), 7.71 (t, 1H, pyrimidine, J = 4.9 Hz), 7.40 (d, 1H, pyridazine, J = 9.8 Hz), 5.15 (q, 1H, SCH, J = 6.0 Hz), 3.12-3.60 (m, 4H, piperidyl $NCH_2$), 1.57 (d, 3H, $CH_3$, J = 7.1 Hz), 1.49-1.58 (m, 2H, piperidinyl $CH_2$), 1.38-1.46 (m, 4H, piperidyl $CH_2$). |
| 110 | calculated for $C_{16}H_{18}N_6OS_2$•H was 375.1056 found 375.1066 | 9.37 (d, 1H, thiazole, J = 1.9 Hz), 8.68 (d, 1H, thiazole, J = 1.6 Hz), 7.36 (d, 1H, pyridazine, J = 9.3 Hz), 5.17 (q, 1H, SCH, J = 6.8 Hz), 3.25-3.60 (m, 4H, piperidyl $NCH_2$), 1.61 (d, 3H, $CH_3$, J = 7.0 Hz), 1.39-1.64 (m, 6H, piperidinyl $CH_2$). |
| 111 | calculated for $C_{15}H_{16}N_6OS_2$•H was 361.0900 found 361.0909 | 9.37 (d, 1H, thiazole, J = 2.0 Hz), 8.67 (d, 1H, thiazole, J = 2.0 Hz), 8.37 (d, 1H, pyridazine, J = 9.8 Hz), 7.36 (d, 1H, pyridazine, J = 9.4 Hz), 4.93 (q, 1H, SCH, J = 6.8 Hz), 3.52-3.63 (m, 2H, pyrrolidine $NCH_2$), 3.26-3.37 (m, 2H, pyrrolidine $NCH_2$), 1.69-1.95 (m, 4H, pyrrolidine $NCH_2$), 1.61 (d, 3H, $CH_3$, J = 6.7 Hz). |
| 112 | calculated for $C_{17}H_{21}N_7OS$•H was 372.1601 found 375.1591 | 8.32 (d, 1H, pyridazine, J = 9.8 Hz), 7.73 (d, 1H, pyrazole, J = 2.0 Hz), 7.39 (d, 1H, pyridazine, J = 9.3 Hz), 7.18 (d, 1H, pyrazole, J = 2.0 Hz), 5.17 (q, 1H, SCH, J = 7.0 Hz), 4.25 (s, 3H, $NCH_3$), 3.51-3.61 (m, 2H, piperidyl $NCH_2$), 3.28-3.42 (m, 2H, piperidyl $NCH_2$), 1.59 (d, 3H, $CH_3$, J = 7.0 Hz), 1.40-1.64 (m, 6H, piperidinyl $CH_2$). |
| 113 | calculated for $C_{17}H_{21}N_7OS_2$•H was 372.1601 found 375.1593 | 8.24 (d, 1H, pyridazine, J = 9.8 Hz), 7.98 (d, 1H, pyrazole, J = 1.9 Hz), 7.29 (d, 1H, pyridazine, J = 9.4 Hz), 7.03 (d, 1H, pyrazole, J = 1.9 Hz), 5.17 (q, 1H, SCH, J = 6.9 Hz), 4.00 (s, 3H, $NCH_3$), 3.24-3.62 (m, 4H, piperidyl $NCH_2$), 1.62 (d, 3H, $CH_3$, J = 7.1 Hz), 1.40-1.64 (m, 6H, piperidinyl $CH_2$). |
| 114 | calculated for $C_{16}H_{17}N_5OS_2$•H was 360.0947 found 340.0943 | 8.28 (d, 1H, pyridazine, J = 9.7 Hz), 8.15 (d d, 1H, thienyl, J = 1.2, 3.5 Hz), 7.92 (d d, 1H, thienyl, J = 1.2, 5.1 Hz), 7.36 (d d, 1H, thienyl, J = 3.6, 5.1 Hz), 7.35 (d, 1H, pyridazine, J = 9.4 Hz), 4.67 (d d, 1H, SCH, J = 6.3, 7.9 Hz), 4.20-4.36 (m, 2H, azetidinyl $NCH_2$), 3.88-3.96 (m, 2H, azetidinyl $NCH_2$), 2.13-2.29 (m, 2H, azetidinyl $CH_2$), 1.72-2.10 (m, 3H, Pr $CH_2$), 1.02 (t, 3H, $CH_3$, J = 5.5 Hz). |

-continued

| Example | MS | NMR |
|---|---|---|
| 115 | calculated for C16H19N7OS•H was 358.1445 found 358.1438 | 8.22 (d, 1H, pyridazine, J = 9.8 Hz), 8.01 (br s, 1H, pyrazole CH), 7.30 (d, 1H, pyridazine, J = 9.7 Hz), 7.08 (br s, 1H, pyrazole CH), 5.16 (q, 1H, SCH, J = 6.8 Hz), 3.30-3.62 (m, 4H, piperidyl $NCH_2$), 1.60 (d, 3H, $CH_3$, J = 7.0 Hz), 1.41-1.68 (m, 6H, piperidinyl $CH_2$). |
| 116 | calculated for $C_{17}H_{19}N_7OS$•H was 370.1445 found 370.1438 | 10.09 (d d, 1H, pyridazine, J = 1.1, 1.9 Hz), 9.51 (d d, 1H, pyridazine, J = 1.2, 5.5 Hz), 8.53 (d d, 1H, pyridazine, J = 2.3, 5.5 Hz), 8.39 (d, 1H, pyridazine, J = 9.8 Hz), 7.47 (d, 1H, pyridazine, J = 9.8 Hz), 5.16 (q, 1H, SCH, J = 6.9 Hz), 3.15-3.66 (m, 4H, piperidyl $NCH_2$), 1.65 (d, 3H, $CH_3$, J = 7.0 Hz), 1.41-1.65 (m, 6H, piperidinyl $CH_2$). |
| 117 | calculated for $C_{16}H_{19}N_5OS_2$•H was 362.1104 found 362.1101 | 8.28 (d, 1H, pyridazine, J = 9.7 Hz), 8.13 (d d, 1H, thienyl, J = 1.1, 3.5 Hz), 7.91 (d d, 1H, thienyl, J = 1.2, 4.7 Hz), 7.35 (d d, 1H, thienyl, J = 3.9, 5.0 Hz), 7.34 (d, 1H, pyridazine, J = 9.8 Hz), 5.17 (q, 1H, SCH, J = 6.7 Hz), 3.40-3.51 and 3.30-3.38 (2m, 4H, $NCH_2$), 1.70 (d, 3H, $CH_3$, J = 6.7 Hz), 1.18 (t, 3H, $CH_3$, J = 7.1 Hz), 1.04 (t, 3H, $CH_3$, J = 7.1 Hz). |
| 118 | calculated for $C_{14}H_{15}N_5OS_2$•H was 334.0791 found 334.0785 | 8.27 (d, 1H, pyridazine, J = 9.7 Hz), 8.12 (d d, 1H, thienyl, J = 1.1, 3.9 Hz), 7.89 (d d, 1H, thienyl, J = 1.2, 5.1 Hz), 7.35 (d d, 1H, thienyl, J = 3.5, 4.6 Hz), 7.34 (d, 1H, pyridazine, J = 9.7 Hz), 5.17 (q, 1H, SCH, J = 6.9 Hz), 3.17 (s, 3H, $NCH_3$), 2.90 (s, 3H, $NCH_3$), 1.66 (d, 3H, $CH_3$, J = 7.1 Hz). |
| 119 | calculated for $C_{13}H_{13}N_5OS_2$•H was 320.0634 found 340.0630 | 8.34-8.40 (m, 1H, C(═O)NH), 8.27 (d, 1H, pyridazine, J = 9.8 Hz), 8.18 (d d, 1H, thienyl, J = 1.1, 5.0 Hz), 7.86 (d d, 1H, thienyl, J = 1.1, 5.0 Hz), 7.33 (d d, 1H, thienyl, J = 3.5, 5.0 Hz), 7.33 (d, 1H, pyridazine, J = 9.4 Hz), 4.63 (q, 1H, SCH, J = 7.0 Hz), 2.62 (d, 3H, $NCH_3$, J = 4.3 Hz), 1.65 (d, 3H, $CH_3$, J = 7.1 Hz). |
| 120 | calculated for $C_{17}H_{21}N_7OS$•H was 372.1601 found 372.1603 | 8.30 (d, 1H, pyridazine, J = 9.4 Hz), 7.51 (br s, 1H, imidazole), 7.35 (d, 1H, pyridazine, J = 9.8 Hz), 7.21 (s, 1H, imidazole), 5.18 (q, 1H, SCH, J = 7.1 Hz), 3.91 (s, 3H, imidazole $CH_3$), 3.20-3.65 (m, 6H, piperidyl), 1.52 (d, 3H, $CH_3$, J = 6.6 Hz). |
| 121 | calculated for $C_{15}H_{17}N_5OS_2$•H was 348.0947 found 348.0949 | 8.28 (d, 1H, pyridazine, J = 9.8 Hz), 8.12 (d d, 1H, thienyl, J = 1.2, 3.5 Hz), 7.91 (d d, 1H, thienyl, J = 1.2, 5.1 Hz), 7.35 (d d, 1H, thienyl, J = 3.5, 5.1 Hz), 7.43 (d, 1H, pyridazine, J = 9.4 Hz), 5.13 (d d, 1H, SCH, J = 5.8, 7.0 Hz), 3.15 (s, 3H, $CH_3$), 2.91 (s, 3H, $CH_3$), 1.97-2.16 (m, 3H, $CH_2$), 1.01 (t, 3H, $CH_3$, J = 7.2 Hz). |
| 127 | calculated for $C_{19}H_{23}N_5OS_2$•H was 402.1416 found 402.1420 | 8.26-8.3 (m, 1H, pyridazine), 8.11-8.16 (m, 1H, thienyl), 7.91-7.92 (m, 1H, thienyl), 7.33-7.36 (m, 2H, thienyl and pyridazine), 5.14-5.26 (m, 1H, SCH), 3.85-4.3 (2m, 2H, $NCH_2$), 1.97-2.15 and 2.32-3.26 (3m, 4H, $NCH_2$ and $CH_2$), 1.09-1.79 (m, 5H, $2CH_2$ and CH), 0.97-1.02 (m, 3H, $CH_3$), 0.65-0.87 (m, 3H, $CH_3$). |
| 122 | calculated for $C_{14}H_{15}N_5OS_2$ was 350.0947 found 350.0949 | 8.48 (m, 1H, NH), 8.26 (d, 1H, pyridazine, J = 9.8 Hz), 8.20 (d d, 1H, thienyl, J = 0.8, 3.5 Hz), 7.86 (d d, 1H, thienyl, J = 1.1, 5.0 Hz), 7.32-7.36 (m, 1H, thienyl), 7.32 (d, 1H, pyridazine, J = 9.4 Hz), 4.66-4.73 (m, 2H, SCH and OH), 3.39 (q, 2H, $CH_2$, J = 5.9 Hz), 3.09-3.22 (app heptet, 2H, $CH_2$), 1.66 (d, 3H, $CH_3$, J = 6.6 Hz). |
| 123 | calculated for $C_{18}H_{23}N_5OS_2$ was 390.1417 found 390.1408 | 8.28 (d, 1H, pyridazine, J = 9.8 Hz), 8.12 (d d, 1H, thienyl, J = 1.2, 3.5 Hz), 7.90 (d d, 1H, thienyl, J = 1.2, 5.1 Hz), 7.34-7.37 (m, 1H, thienyl), 7.34 (d, 1H, pyridazine, J = 9.4 Hz), 5.14 (q, H, SCH, J = 6.7 Hz), 3.20-3.37 (m, 4H, $NCH_2$), 1.71 (d, 3H, $CH_3$, J = 6.6 Hz), 1.52-1.65 (m, 2H, $CH_2$), 1.50 (sextet, 2H, $CH_2$, J = 7.4 Hz), 0.83 (t, 3H, $CH_3$, J = 7.5 Hz), 0.75 (t, 3H, $CH_3$, J = 7.4 Hz). |
| 125 | calculated for $C_{16}H_{18}N_6OS_2$ was 375.1068 found 375.1060 | 8.37 (d, 1H, pyridazine, J = 9.7 Hz), 8.20 (d, 1H, thienyl, J = 3.1 Hz), 8.15 (d, 1H, thienyl, J = 3.1 Hz), 7.45 (d, 1H, pyridazine, J = 9.8 Hz) 5.30 (q, 1H, SCH, J = 6.8 Hz), 3.54-3.59 (m, 1H, $NCH_2$), 3.46-3.51 (m, 1H, $NCH_2$), 1.68 (d, 3H, $CH_3$, J = 6.6 Hz), 1.50-1.65 (m, 1H, $CH_2$), 1.41-1.52 (m, 1H, $CH_2$). |
| 126 | calculated for $C_{14}H_{14}N_6OS_2$ was 347.0743 found 347.0749 | 8.38 (d, 1H, pyridazine, J = 9.8 Hz), 8.21 (d, 1H, thienyl, J = 3.2 Hz), 8.14 (d, 1H, thienyl, J = 3.1 Hz), 7.44 (d, 1H, pyridazine, J = 9.3 Hz), 4.84 (q, 1H, SCH, J = 6.8 Hz), 4.24-4.37 (m, 2H, azetidinyl $NCH_2$), 3.88-3.95 (m, 1H, azetidinyl $NCH_2$), 2.15-2.28 (m, 2H, azetidinyl $NCH_2$), 1.63 (d, 3H, $NCH_3$, J = 6.6 Hz). |

Preparation of 6-chloro-3-(2-fluorophenyl)-[1,2,4]triazolo[4,3-b]pyridazine

6-Chloro-3-hydrazinopyridazine (6.9 mmol) was suspended in dioxane (45 mL) with triethylamine (1.1 equiv), and the acyl chloride of 2-fluorobenzoic acid (1.1 equiv) in dioxane (10 ml) was added dropwise over 5-10 min at room temperature. The reaction mixture was stirred at the same temperature for 30-50 min (monitored by TLC), and then the dioxane was removed by rotary evaporation. The residue was refluxed in phosphorus oxychloride (40 ml) for 3-4 hours, and then the solvent was evaporated. 6-Chloro-3-(2-fluorophenyl)-[1,2,4]triazolo[4,3-b]pyridazine was obtained by washing the residue several times with ethyl acetate followed by filtration then adding ice-cold water (50 ml) to the residue. The aqueous layer was neutralized to pH 7 with saturated aqueous sodium hydrogen carbonate, and the resulting solid was collected by filtration, washed twice with water and then with hexane, and dried under vacuum at 50° C. $^1H$ NMR (400 MHz, $Me_2SO-d_6$): 8.57 (d, 1H, pyridazine, J=9.3 Hz), 7.85-7.89 (td, 1H, Ph, J=1.6 Hz and 7.4 Hz), 7.68-7.72 (m, 1H, Ph), 7.58 (d, 1H, pyridazine, J=9.4 Hz), 7.45-7.53 (m, 2H, Ph). FABMS (M+H) calculated for $C_{11}H_6ClFN_4$.H was 249.0337. found 249.0339.

The following compounds were prepared by this method:

a) 6-Chloro-3-(3-fluorophenyl)-[1,2,4]triazolo[4,3-b]pyridazine:

$^1H$ NMR (400 MHz, $Me_2SO-d_6$): 8.57 (d, 1H, pyridazine, J=9.8 Hz), 8.17-8.2 (m, 1H, Ph), 8.08-8.12 (m, 1H, Ph), 7.68-7.73 (m, 1H, Ph), 7.6 (d, 1H, pyridazine, J=9.4 Hz), 7.43-7.48 (m, 1H, Ph). FABMS (M+H) calculated for $C_{11}H_6ClFN_4$.H was 249.0337. found 249.0342.

b) 6-Chloro-3-(4-fluorophenyl)-[1,2,4]triazolo[4,3-b]pyridazine:

$^1$H NMR (400 MHz, $Me_2SO$-$d_6$): 8.6 (d, 1H, pyridazine, J=9.4 Hz), 8.55 (d, 2H, Ph, J=7.9 Hz), 8.03 (d, 2H, Ph, J=8.3 Hz), 7.62 (d, 1H, pyridazine, J=9.4 Hz). FABMS (M+H) calculated for $C_{12}H_6ClF_3N_4$.H was 299.0306. found 299.0310.

c) 6-Chloro-3-(3,4-difluorophenyl)-[1,2,4]triazolo[4,3-b]pyridazine:

$^1$H NMR (400 MHz, $Me_2SO$-$d_6$): 8.57 (d, 1H, pyridazine, J=9.4 Hz), 8.28-8.34 (m, 1H, Ph), 8.18-8.22 (m, 1H, Ph), 7.71-7.78 (m, 1H, Ph), 7.6 (d, 1H, pyridazine, J=9.8 Hz).

FABMS (M+H) calculated for $C_{11}H_5ClF_2N_4$.H was 267.0243. found 267.0249.

FABMS (M+H) calculated for $C_9H_5ClN_4S$.H was 236.9996. found 236.9993.

d) 6-Chloro-3-(4-methoxyphenyl)-[1,2,4]triazolo[4,3-b]pyridazine

FABMS (M+H) calculated for $C_{12}H_9ClN_4O$.H was 261.0538. found 261.0541.

e) 6-Chloro-3-(3-methoxyphenyl)-[1,2,4]triazolo[4,3-b]pyridazine f) 6-Chloro-3-(2-methoxyphenyl)-[1,2,4]triazolo[4,3-b]pyridazine Preparation of 3-(2-fluorophenyl)-[1,2,4]triazolo[4,3-b]pyridazine-6-thiol A solution of 6-chloro-3-(2-fluorophenyl)-[1,2,4]triazolo[4,3-b]pyridazine (1 mmol) and sodium hydrosulfide hydrate (1.5 equiv.) in ethanol was refluxed for 2-6 hours. The solvent was removed under reduced pressure, water (2 ml) was added, and the pH adjusted to 9 with sodium hydroxide solution. After removing the resulting precipitate, the filtrate was acidified with 6M HCl to a pH of 3, and the formed precipitate was collected, washed with cold water, and dried to give 3-(2-fluorophenyl)-[1,2,4]triazolo[4,3-b]pyridazine-6-thiol. This compound is taken on to the next step without purification Example 74

Ethyl 2-((3-(2-fluorophenyl)-[1,2,4]triazolo[4,3-b]pyridazin-6-yl)thio)butanoate To a solution of 3-(2-fluorophenyl)-[1,2,4]triazolo[4,3-b]pyridazine-6-thiol (1 mmol) and cesium carbonate (1.5 equiv.) in DMF (5 mL) was added ethyl 2-bromobutyrate (1.5 equiv.) and the mixture was stirred at 70° C. for 3 hours. The reaction was monitored by thin-layer chromatography and was shown to be complete at this time. The solvent was removed in vacuo and the residue was chromatographed on a silica gel column, to furnish ethyl 2-((3-(2-fluorophenyl)-[1,2,4]triazolo[4,3-b]pyridazin-6-yl)thio)butanoate.

The following compounds were prepared by adaptation of the method used above:

| Example | MS | NMR |
|---|---|---|
| 74 | calculated for $C_{17}H_{17}FN_4O_2S$•H was 361.1129 found 361.1137 | 8.32 (d, 1H, pyridazine, J = 9.7 Hz), 7.86-7.95 (td, 1H, Ph, J = 2 Hz and 7.4 Hz), 7.67-7.72 (m, 1H, Ph), 7.48-7.51 (m, 1H, Ph), 7.42-7.46 (td, 1H, Ph, J = 1.2 Hz and 7.9 Hz), 7.4 (d, 1H, pyridazine, J = 9.8 Hz), 4.29 (t, 1H, SCH, J = 6.8 Hz), 4-4.08 (dq, 1H, OCH, J = 7 Hz and 10.6 Hz), 3.8-3.88 (dq, 1H, OCH, J = 7 Hz and 10.9 Hz), 1.9-1.96 (dq, 2H, $CH_2$, J = 7 Hz and 3.1 Hz), 1.02 (t, 3H, $CH_3$, J = 7.5 Hz), 0.94 (t, 3H, $CH_3$, J = 7.4 Hz). |
| 75 | calculated for $C_{17}H_{17}FN_4O_2S$•H was 361.1129 found 361.1141 | 8.33 (d, 1H, pyridazine, J = 9.8 Hz), 8.14-8.2 (m, 2H, Ph), 7.63-7.69 (td, 1H, Ph, J = 5.8 Hz and 2 Hz), 7.41-7.46 (m, 1H, Ph), 7.4 (d, 1H, pyridazine, J = 9.8 Hz), 4.55 (t, 1H, SCH, J = 6.8 Hz), 3.96-4.04 and 4.09-4.17 (2dq, 2H, $OCH_2$, J = 7.1 Hz and 11 Hz), 2.01-2.09 (m, 2H, $CH_2$), 1.07 (t, 3H, $CH_3$, J = 7 Hz), 1.05 (t, 3H, $CH_3$, J = 7.4 Hz). |
| 76 | calculated for $C_{17}H_{16}F_2N_4O_2S$•H was 379.1034 found 379.1042. | 8.35-8.5 (m, 1H, Ph), 8.32 (d, 1H, pyridazine, J = 9.8 Hz), 8.17-8.22 (m, 1H, Ph), 7.65-7.72 (m, 1H, Ph), 7.41 (d, 1H, pyridazine, J = 9.8 Hz), 4.54 (t, 1H, SCH, J = 7.5 Hz), 4.09-4.17 and 3.97-4.5 (2dq, 2H, $OCH_2$, J = 7 Hz and 10.7 Hz), 2-2.08 (m, 2H, $CH_2$), 1.06 (t, 3H, $CH_3$, J = 7.2 Hz), 1.04 (t, 3H, $CH_3$, J = 7.4 Hz). |
| 77 | calculated for $C_{18}H_{17}F_3N_4O_2S$•H was 411.1097 found 411.1103 | 8.58 (d, 2H, Ph, J = 8.2 Hz), 8.35 (d, 1H, pyridazine, J = 9.8 Hz), 7.96 (d, 2H, Ph, J = 8.2 Hz), 7.44 (d, 1H, pyridazine, J = 9.7 Hz), 4.57 (t, 1H, SCH, J = 6.8 Hz), 4.06-4.14 and 3.92-4 (2dq, 2H, $OCH_2$, J = 7.1 Hz and 10.6 Hz), 2-2.08 (m, 2H, $CH_2$), 1.05 (t, 3H, $CH_3$, J = 7.4 Hz), 1.03 (t, 3H, $CH_3$, J = 7.2 Hz). |
| 65 | calculated for $C_{18}H_{20}N_4O_3S$•H was 373.1329 found 373.1349 | 8.28-8.32 (d m, 2H, Ph), 8.28 (d, 2H, pyridazine, J = 11.0 Hz), 7.34 (d, 1H, pyridazine, J = 9.7 Hz), 7.15 (d m, 2H, Ph), 4.53 (t, 1H, SCH, J = 6.8 Hz), 4.10-4.18 and 3.97-4.06 (2dq, 2H, $OCH_2$, J = 7.0 Hz and 11.0 Hz), 3.87 (s, 3H, $OCH_3$), 1.99-2.09 (m, 2H, $CH_2$), 1.09 (t, 3H, $CH_3$, J = 7.0 Hz), 1.05 (t, 3H, $CH_3$, J = 7.4 Hz). |
| 68 | calculated for $C_{18}H_{20}N_4O_3S$•H was 373.1329 found 373.1335 | 8.28 (d, 1H, pyridazine, J = 9.8 Hz), 7.59-7.64 (m, 1H, Ph), 7.53 (dd, 1H, Ph, J = 1.5, 7.4 Hz), 7.34 (d, 1H, pyridazine, J = 9.7 Hz), 7.27 (app d, 1H, Ph, J = 7.9 Hz), 7.13 (d t, 1H, Ph, J = 0.7, 7.4 Hz), 4.20 (t, 1H, SCH, J = 6.8 Hz), 3.93-4.02 and 3.68-3.76 (2dq, 2H, $OCH_2$, J = 7.0 Hz and 10.9 Hz), 3.78 (s, 3H, $OCH_3$), 1.82-1.99 (m, 2H, $CH_2$), 1.00 (t, 3H, $CH_3$, J = 7.0 Hz), 0.90 (t, 3H, $CH_3$, J = 7.3 Hz). |
| 71 | calculated for $C_{18}H_{20}N_4O_3S$•H was 373.1329 found 373.1325 | 8.31 (d, 1H, pyridazine, J = 9.8 Hz), 7.92-7.96 (d m, 1H, Ph), 7.86-7.89 (m, 1H, Ph), 7.52 (t, 1H, Ph, J = 8.0 Hz), 7.39 (d, 1H, pyridazine, J = 9.3 Hz), 7.13-7.17 (d m, 1H, Ph), 4.57 (t, 1H, SCH, J = 6.7 Hz), 4.06-4.16 and 3.93-4.02 (2dq, 2H, $OCH_2$, J = 7.1 Hz and 11.0 Hz), 3.89 (s, 3H, $OCH_3$), 1.99-2.09 (m, 2H, $CH_2$), 1.06 (t, 3H, $CH_3$, J = 7.0 Hz), 1.03 (t, 3H, $CH_3$, J = 7.4 Hz). |

Example 55

2-((3-(2-Fluorophenyl)-[1,2,4]triazolo[4,3-b]pyridazin-6-yl)thio)butanoic acid

To a solution of ethyl 2-((3-(2-fluorophenyl)-[1,2,4]triazolo[4,3-b]pyridazin-6-yl)thio)butanoate (1 mmol) in dioxane (3 mL) was added 0.5 ml of sodium hydroxide (2N), and the reaction mixture was stirred at room temperature. After 2 hours, the mixture was evaporated to dryness, and the obtained residue dissolved in water (2 mL) and then acidified with an hydrochloric acid solution. The resulting precipitate was filtered, washed with water, and dried to give 2-((3-(2-fluorophenyl)-[1,2,4]triazolo[4,3-b]pyridazin-6-yl)thio)butanoic acid.

The method above was adapted to give the following compounds:

| Example | MS | NMR |
|---|---|---|
| 53 | calculated for $C_{16}H_{13}F_3N_4O_2S$•H was 383.0784 found 383.0786 | 8.63 (d, 2H, Ph, J = 8.2 Hz), 8.22 (d, 1H, pyridazine, J = 9.8 Hz), 7.94 (d, 2H, Ph, J = 8.6 Hz), 7.31 (d, 1H, pyridazine, J = 9.4 Hz), 4.26 (t, 1H, SCH, J = 5.5 Hz), 1.96-2.07 (m, 2H, $CH_2$), 1 (t, 3H, $CH_3$, J = 7.4 Hz). |
| 54 | calculated for $C_{15}H_{12}F_2N_4O_2S$•H was 351.0721 found 351.0723. | 8.37-8.43 (m, 1H, Ph), 8.24-8.27 (m, 1H, Ph), 8.21 (d, 1H, pyridazine, J = 9.4 Hz), 7.63-7.7 (m, 1H, Ph), 7.29 (d, 1H, pyridazine, J = 9.8 Hz), 4.27 (t, 1H, SCH, J = 5.8 Hz), 1.99-2.05 (m, 2H, $CH_2$), 1.01 (t, 3H, $CH_3$, J = 7.2 Hz). |
| 55 | calculated for $C_{15}H_{13}FN_4O_2S$•H was 333.0816 found 333.0819 | 8.2 (d, 1H, pyridazine, J = 9.4 Hz), 7.89-7.92 (td, 1H, Ph, J = 1.6 Hz and 7.8 Hz), 7.64-7.7 (m, 1H, Ph), 7.41-7.49 (m, 2H, Ph), 7.28 (d, 1H, pyridazine, J = 9.4 Hz), 4.05 (m, 1H, SCH), 1.86-1.98 (m, 2H, $CH_2$), 0.87 (t, 3H, $CH_3$, J = 7.4 Hz). |
| 56 | calculated for $C_{15}H_{13}FN_4O_2S$•H was 333.0816 found 333.0822 | 8.21-8.28 (m, 2H, Ph), 8.13 (d, 1H, pyridazine, J = 9.8 Hz), 7.62-7.68 (td, 1H, Ph, J = 6.2 Hz and 8.2 Hz), 7.38-7.43 (td, 1H, Ph, J = 2.2 Hz and 7.9 Hz), 7.23 (d, 1H, pyridazine, J = 9.4 Hz), 4.13 (dd, 1H, SCH, J = 4.3 Hz and 3.2 Hz), 1.89-2.08 (m, 2H, $CH_2$), 0.96 (t, 3H, $CH_3$, J = 7.4 Hz). |

Example 18

2-((3-(2-Fluorophenyl)-[1,2,4]triazolo[4,3-b]pyridazin-6-yl)thio)butanamide

To 10 ml of dry methanol saturated with ammonia was added 0.5 mmol of ethyl 2-((3-(2-fluorophenyl)-[1,2,4]triazolo[4,3-b]pyridazin-6-yl)thio)butanoate. The pressure tube was stoppered tightly, and the solution was stirred for 16 hours at 50° C. The white precipitate was collected and washed with cold methanol to give 2-((3-(2-fluorophenyl)-[1,2,4]triazolo[4,3-b]pyridazin-6-yl)thio)butanamide.

The following compounds were prepared by adaptation of the method above:

| Example | MS | NMR |
|---|---|---|
| 66 | calculated for $C_{16}H_{17}N_5O_2S$•H was 344.1176 found 344.1185 | 8.32-8.37 (d app t, 2H, Ph, J = 2.9, 12.0 Hz), 8.24 (d, 2H, pyridazine, J = 9.7 Hz), 7.86 (br s, 1H, $NH_2$), 7.36 (br s, 1H, $NH_2$), 7.29 (d, 1H, pyridazine, J = 9.6 Hz), 7.16 (d app t, 2H, Ph, J = 2.1, 12.0 Hz), 4.38 (d d, 1H, SCH, J = 5.6, 7.9 Hz), 3.87 (s, 3H, $OCH_3$), 1.95-2.09 (m, 2H, $CH_2$), 1.03 (t, 3H, $CH_3$, J = 7.4 Hz) |
| 69 | calculated for $C_{16}H_{16}N_4O_3S$•H was 344.1176 found 344.1172 | 8.24 (d, 1H, pyridazine, J = 9.7 Hz), 7.61-7.64 (m, 1H, $NH_2$), 7.61-7.62 (m, 1H, Ph), 7.55-7.59 (m, 1H, Ph), 7.29 (d, 1H, pyridazine, J = 9.8 Hz), 7.24 (d, 1H, Ph, J = 8.6 Hz), 7.23 (br s, 1H, $NH_2$), 7.13 (d t, 1H, Ph, J = 0.7, 7.4 Hz), 4.03 (dd, 1H, SCH, J = 5.4, 8.2 Hz), 3.77 (s, 3H, $OCH_3$), 1.83-1.95 (m, 2H, $CH_2$), 0.81 (t, 3H, $CH_3$, J = 7.4 Hz) |
| 72 | calculated for $C_{16}H_{16}N_4O_3S$•H was 344.1176 found 345.1162 | 8.27 (d, 1H, pyridazine, J = 9.4 Hz), 8.02-8.06 (d m, 1H, Ph), 7.86 (d d, 1H, Ph, J = 1.6, 2.7 Hz), 7.85 (br s, 1H, $NH_2$), 7.54 (t, 1H, Ph, J = 8.0 Hz), 7.34 (br s, 1H, $NH_2$), 7.33 (d, 1H, pyridazine, J = 9.7 Hz), 7.14-7.18 (d m, 1H, Ph), 4.38 (d d, 1H, SCH, J = 5.4, 8.6 Hz), 3.87 (s, 3H, $OCH_3$), 1.94-2.10 (m, 2H, $CH_2$), 1.01 (t, 3H, $CH_3$, J = 7.5 Hz). |
| 78 | calculated for $C_{16}H_{14}F_3N_5OS$•H was 382.0943 found 382.0945 | 8.64 (d, 2H, Ph, J = 8.2 Hz), 8.31 (d, 1H, pyridazine, J = 9.8 Hz), 7.97 (d, 2H, Ph, J = 8.2 Hz), 7.86 (br s, NH), 7.38-7.7.4 (m, 2H, pyridazine and NH), 4.4 (t, 1H, SCH, J = 6.6 Hz), 1.99-2.03 (m, 2H, $CH_2$), 1.02 (t, 3H, $CH_3$, J = 7.4 Hz). |
| 79 | calculated for $C_{15}H_{13}F_2N_5OS$•H was 350.0881 found 350.0888. | 8.34-8.39 (m, 1H, Ph), 8.28-8.30 (d, 1H, pyridazine, J = 9.8 Hz and br s, 1H, Ph), 7.83 (br s, 1H, NH), 7.65-7.72 (m, 1H, Ph), 7.35-7.37 (d, 1H, pyridazine, J = 9.7 Hz and br s, 1H, NH), 4.37 (t, 1H, SCH, J = 6.8 Hz), 1.98-2.04 (m, 2H, $CH_2$), 1.01 (t, 3H, $CH_3$, J = 7.4 Hz). |
| 80 | calculated for $C_{15}H_{14}FN_5OS$•H was 332.0975 found 332.0983 | 8.28 (d, 1H, pyridazine, J = 9.3 Hz), 7.93-7.97 (td, 1H, Ph, J = 2 Hz and 7.5 Hz), 7.66-7.71 (m, 2H, Ph and NH), 7.43-7.5 (m, 2H, Ph), 7.34 (d, 1H, pyridazine, J = 9.4 Hz), 4.26 (brs, 1H, NH), 4.13-4.16 (dd, SCH, J = 4.7 Hz and 8.6 Hz), 1.86-2 (m, 2H, $CH_2$), 0.88 (t, 3H, $CH_3$, J = 7.2 Hz). |

-continued

| Example | MS | NMR |
|---|---|---|
| 81 | calculated for $C_{15}H_{14}FN_5OS{\bullet}H$ was 332.0975 found 332.0979 | 8.29 (d, 1H, pyridazine, J = 9.8 Hz), 8.27 (d, 1H, Ph, J = 8.3 Hz), 8.14-8.17 (m, 1H, Ph), 7.87 (br s, 1H, NH), 7.64-7.7 (m, 1H, Ph), 7.4-7.46 (td, 1H, Ph, J = 2 Hz and 8.2 Hz), 7.35-7.7.37 (m, 2H, pyridazine and NH), 4.37-4.41 (dd, SCH, J = 5.5 Hz and 8.6 Hz), 1.95-2.1 (m, 2H, $CH_2$), 1.02 (t, 3H, $CH_3$, J = 7.4 Hz). |

Example 94

2-((3-(2-Fluorophenyl)-[1,2,4]triazolo[4,3-b]pyridazin-6-yl)thio)-1-(piperidin-1-yl)butan-1-one To a solution of 3-(2-fluorophenyl)-[1,2,4]triazolo[4,3-b]pyridazine-6-thiol (1 mmol) and cesium carbonate (1.5 equiv.) in DMF (5 mL) was added 2-bromo-1-(piperidin-1-yl)butan-1-one (1.5 equiv.) and the mixture was stirred at 70° C. for 3 hours. The reaction was monitored by thin-layer chromatography and was shown to be complete at this time. The solvent was removed in vacuo and the residue was flash chromatographed to give 2-((3-(2-fluorophenyl)-[1,2,4]triazolo[4,3-b]pyridazin-6-yl)thio)-1-(piperidin-1-yl)butan-1-one.

The following compounds were prepared by an adaptation of the method above:

Example 51

1-(3-Methylpiperidin-1-yl)-2-((3-(thiophen-2-yl)-[1,2,4]triazolo[4,3-b]pyridazin-6-yl)thio)butan-1-one $^1$H NMR (400 MHz, $Me_2SO-d_6$): 8.26-8.3 (m, 1H, pyridazine), 8.11-8.16 (m, 1H, thienyl), 7.91-7.92 (m, 1H, thienyl), 7.33-7.36 (m, 2H, thienyl and pyridazine), 5.14-5.26 (m, 1H, SCH), 3.85-4.3 (2m, 2H, $NCH_2$), 1.97-2.15 and 2.32-3.26 (3m, 4H, $NCH_2$ and $CH_2$), 1.09-1.79 (m, 5H, $2CH_2$ and CH), 0.97-1.02 (m, 3H, $CH_3$), 0.65-0.87 (m, 3H, $CH_3$). FABMS (M+H) calculated for $C_{19}H_{23}N_5OS_2$.H was 402.1416. found 402.1420.

| Example | MS | NMR |
|---|---|---|
| 67 | calculated for $C_{21}H_{25}N_5O_2S{\bullet}H$ was 412.1802 found 412.1809 | 8.25-8.30 (d app t, 2H, Ph, J = 2.7, 11.7 Hz), 8.24 (d, 2H, pyridazine, J = 10.2 Hz), 7.30 (d, 1H, pyridazine, J = 9.8 Hz), 7.16 (d app t, 2H, Ph, J = 2.7, 9.0 Hz), 5.03 (d d, 1H, SCH, J = 5.6, 7.5 Hz), 3.86 (s, 3H, $OCH_3$), 3.50-3.60 (m, 2H, $NCH_2$), 3.32-3.46 (m, 2H, $NCH_2$), 2.05-2.13 (m, 1H, $CH_2$), 1.93-2.03 (m, 2H, $CH_2$), 1.39-1.66 (m, 6H, $CH_2CH_2CH_2$), 0.97 (t, 3H, $CH_3$, J = 7.3 Hz). |
| 70 | calculated for $C_{21}H_{25}N_5O_2S{\bullet}H$ was 412.1802 found 412.1783 | 8.25 (d, 1H, pyridazine, J = 9.8 Hz), 7.60-7.65 (m, 1H, Ph), 7.55 (d d, 1H, Ph, J = 2.0, 7.8 Hz), 7.29 (d, 1H, pyridazine, J = 9.8 Hz), 7.28 (d, 1H, Ph, J = 8.2 Hz), 7.15 (d t, 1H, Ph, J = 0.8, 7.5 Hz), 4.70 (dd, 1H, SCH, J = 5.9, 7.4 Hz), 3.77 (s, 3H, $OCH_3$), 3.50-3.58 (m, 1H, $NCH_2$), 3.26-3.34 (m, 1H, $NCH_2$), 3.10-3.18 (m, 1H, $NCH_2$), 2.88-2.97 (m, 1H, $NCH_2$), 1.84-1.96 (m, 1H, $CH_2$), 1.68-1.79 (m, 1H, $CH_2$), 1.15-1.59 (m, 5H, $CH_2CH_2CH_2$), 0.79 (t, 3H, $CH_3$, J = 7.2 Hz). |
| 73 | calculated for $C_{21}H_{25}N_5O_2S{\bullet}H$ was 412.1802 found 412.1809 | 8.28 (d, 1H, pyridazine, J = 9.3 Hz), 7.92-7.94 (m, 1H, Ph), 7.90-7.92 (m, 1H, Ph), 7.52-7.57 (m, 1H, Ph), 7.34 (d, 1H, pyridazine, J = 9.4 Hz), 7.16-7.20 (d m, 1H, Ph), 5.09 (d d, 1H, SCH, J = 5.5, 7.4 Hz), 3.86 (s, 3H, $OCH_3$), 3.54-3.66 (m, 1H, $NCH_2$), 3.38-3.47 (m, 1H, $NCH_2$), 1.94-2.12 (m, 2H, $CH_2$), 1.37-1.68 (m, 5H, $CH_2CH_2CH_2$), 0.96 (t, 3H, $CH_3$, J = 7.5 Hz). |
| 94 | calculated for $C_{20}H_{22}FN_5OS{\bullet}H$ was 400.1601 found 400.1612 | 8.30 (d, 1H, pyridazine, J = 9.4 Hz), 7.88-7.92 (td, 1H, Ph, J = 1.9 Hz and 7.4 Hz), 7.68-7.74 (m, 1H, Ph), 7.5-7.53 (m, 1H, Ph), 7.44-7.48 (td, 1H, Ph, J = 1.2 Hz and 7.8 Hz), 7.35 (d, 1H, pyridazine, J = 9.8 Hz), 4.85 (dd, SCH, J = 5.8 Hz and 7.4 Hz), 3.53-3.58 and 3.38-3.41 (2m, 2H, $NCH_2$), 3.2-3.26 and 3.11-3.16 (2m, 2H, $NCH_2$), 1.91-1.98 and 1.76-1.83 (2m, 2H, $CH_2$), 1.3-1.57 (m, 6H, $3CH_2$), 0.82 (t, 3H, $CH_3$, J = 7.4 Hz). |
| 95 | calculated for $C_{21}H_{22}F_3N_5OS{\bullet}H$ was 450.1569 found 450.1576 | 8.54 (d, 2H, Ph, J = 7.8 Hz), 8.33 (d, 1H, pyridazine, J = 9.8 Hz), 7.99 (d, 2H, Ph, J = 8.6 Hz), 7.39 (d, 1H, pyridazine, J = 9.4 Hz), 5.03 (dd, SCH, J = 5.9 Hz and 6.5 Hz), 3.39-3.54 (2m, 4H, $NCH_2$), 1.95-2.11 (m, 2H, $CH_2$), 1.42-1.6 (2m, 6H, $3CH_2$), 0.96 (t, 3H, $CH_3$, J = 7.2 Hz). |
| 96 | calculated for $C_{20}H_{21}F_2N_5OS{\bullet}H$ was 418.1507 found 418.1504 | 8.39-8.45 (m, 1H, Ph), 8.3 (d, 1H, pyridazine, J = 9.8 Hz), 8.16-8.2 (m, 1H, Ph), 7.69-7.76 (m, 1H, Ph), 7.37 (d, 1H, pyridazine, J = 9.8 Hz), 5.07 (dd, SCH, J = 5.5 Hz and 7.4 Hz), 3.36-3.62 (2m, 2H, $NCH_2$), 1.97-2.12 (m, 2H, $CH_2$), 1.44-1.63 (m, 6H, $3CH_2$), 0.95 (t, 3H, $CH_3$, J = 7.5 Hz). |
| 97 | calculated for $C_{20}H_{22}FN_5OS{\bullet}H$ was 400.1601 found 400.1586 | 8.3 (d, 1H, pyridazine, J = 9.8 Hz), 8.16-8.22 (m, 2H, Ph), 7.65-7.7 (td, 1H, Ph, J = 6.3 Hz and 8.2 Hz), 7.4-7.47 (m, 1H, Ph), 7.36 (d, 1H, pyridazine, J = 9.8 Hz), 5.08 (dd, SCH, J = 5.4 Hz and 7.8 Hz), 3.55-3.64 (m, 2H, CHNCH), 3.31-3.44 (m, 2H, CHNCH), 1.97-2.13 (m, 2H, $CH_2$), 1.4-1.63 (m, 6H, $3CH_2$), 0.95 (t, 3H, $CH_3$, J = 6.7 Hz) |

Example 52

N-Cyclohexyl-2-((3-(thiophen-2-yl)-[1,2,4]triazolo[4,3-b]pyridazin-6-yl)thio)butanamide $^1$H NMR (400 MHz, $Me_2SO-d_6$): 8.31 (d, 1H, NH, J=7.8 Hz), 8.25 (d, 1H, pyridazine, J=9.8 Hz), 8.2 (dd, 1H, thienyl, J=1.2 Hz and 3.9 Hz), 7.88 (dd, 1H, thienyl, J=1.1 Hz and 5.1 Hz), 7.34 (dd, 1H, thienyl, J=3.5 and 5.1 Hz), 7.31 (d, 1H, pyridazine, J=9.4 Hz), 4.5 (dd, 1H, SCH, J=5 Hz and 9 Hz), 3.51-3.56 (m, 1H, NCH), 1.95-2.14 (2m, 2H, $CH_2$), 1.08-1.76 (4m, 10H, $5CH_2$), 1.02 (t, 3H, $CH_3$, J=7.2 Hz). FABMS (M+H) calculated for $C_{19}H_{23}N_5OS_2$.H was 402.1416. found 402.1423.

Example 106

2-((3-Phenyl-[1,2,4]triazolo[4,3-b]pyridazin-6-yl)thio)-1-(piperidin-1-yl)butan-1-one HPLC 99.8%, Column: Bondclon C18, $t_R$=8.8 minutes, $H_3CCN/H_2O$ (40-90%). $^1$H NMR (400 MHz, $Me_2SO-d_6$): 8.33 (d d, 2H, Ph, J=2 and 3.9 Hz), 8.28 (d, 1H, pyridazine, J=9.4 Hz), 7.58-7.64 (m, 3H, Ph), 7.33 (d, 1H, pyridazine, J=9.8 Hz), 5.03 (d d, SCH, J=5.5 and 7.8 Hz), 3.36-3.42 and 3.51-3.6 (2 m, 4H, $NCH_2$), 1.94-2.11 and 1.43-1.6 (2 m, 4H, $4CH_2$), 0.95 (t, 3H, $CH_3$, J=7.4 Hz). FABMS (M+H) calculated for $C_{20}H_{23}N_5OS$.H was 382.1696. found 382.1695.

Example 82

Ethyl 2-((3-(thiophen-2-yl)-[1,2,4]triazolo[4,3-b]pyridazin-6-yl)oxy)butanoate

Sodium hydride (1.5 equiv., 60% in mineral oil) was added at 0° C. to a solution of ethyl 2-hydroxybutyrate (1.5 equiv.) in dry DMF (7 mL) under argon atmosphere and the mixture was stirred for 10 min. To this mixture was added 6-chloro-3-(thiophen-2-yl)-[1,2,4]triazolo[4,3-b]pyridazine (1 mmol) dissolved in DMF (3 mL). After 30 min, TLC showed that all the staring material was consumed. The solution was extracted with ethyl acetate, washed with water twice and concentrated. The crude syrup thus obtained was purified by flash column chromatography to give ethyl 2-((3-(thiophen-2-yl)-[1,2,4]triazolo[4,3-b]pyridazin-6-yl)oxy)butanoate.

$^1$H NMR (400 MHz, $Me_2SO-d_6$): 8.4 (d, 1H, pyridazine, J=9.8 Hz), 8.06 (dd, 1H, thienyl, J=1.2 Hz and 3.5 Hz), 7.86 dd, 1H, thienyl, J=1.2 Hz and 5.1 Hz), 7.32 (dd, 1H, thienyl, J=3.9 Hz and 5.1 Hz), 7.25 (d, 1H, pyridazine, J=9.8 Hz), 5.26 (dd, 1H, SCH, J=5.4 Hz and 7 Hz), 4.09-4.21 (m, 2H, $OCH_2$), 1.96-2.09 (m, 2H, $CH_2$), 1.16 (t, 3H, $CH_3$, J=7.2 Hz), 1.07 (t, 3H, $CH_3$, J=5.6 Hz). FABMS (M+H) calculated for $C_{15}H_{16}N_4O_3S$.H was 333.1015. found 333.1022.

Example 83

2-((3-(Thiophen-2-yl)-[1,2,4]triazolo[4,3-b]pyridazin-6-yl)oxy)butanoic acid

To a solution of ethyl 2-((3-(thiophen-2-yl)-[1,2,4]triazolo[4,3-b]pyridazin-6-yl)oxy)butanoate. (1 mmol) in dioxane (3 mL) was added 0.5 ml of sodium hydroxide (2N), and the reaction mixture was stirred at room temperature. After 2 hours, the mixture was evaporated to dryness, and the obtained residue dissolved in water (2 mL) and then acidified with a hydrochloric acid solution. The resulting precipitate was filtered, washed with water, and dried to give 2-((3-(thiophen-2-yl)-[1,2,4]triazolo[4,3-b]pyridazin-6-yl)oxy)butanoic acid.

$^1$H NMR (400 MHz, $Me_2SO-d_6$): 8.3 (d, 1H, pyridazine, J=9.8 Hz), 8.17 (d, 1H, thienyl, J=2.7 Hz), 7.79 (dd, 1H, thienyl, J=0.8 Hz and 5.1 Hz), 7.26 (dd, 1H, thienyl, J=5.6 Hz and 5.1 Hz), 7.15 (d, 1H, pyridazine, J=9.8 Hz), 5.04 (br m, 1H, OCH), 1.94-1.99 (m, 2H, $CH_2$), 1.04 (t, 3H, $CH_3$, J=7.4 Hz). FABMS (M+H) calculated for $C_{13}H_{12}N_4O_3S$.H was 305.0702. found 305.0705.

Biological Testing

Compounds were assessed for inhibition of LRRK2 inhibition using the following procedure.

Recombinant GST-LRRK2 (delta970), purified from baculovirus infected insect cells (SF9), at least 90% pure and either wild-type sequence or bearing the pathogenic G2019S mutation, was combined into a kinase buffer at 30 nM concentration. Kinase buffer consists of 50 mM Tris HCl pH 7.4, 1 mM EDTA, and 50 μM peptide substrate (amino acid sequence RLGAWRFYTLRRARQGNTKQR). Experimental compounds or control (no compound) were added at desired concentrations in DMSO and water, where final concentration of DMSO in kinase reactions was 0.1% for all drug concentrations. Activation buffer that consists of a final concentration in the reactions of 10 mM $MgCl_2$ and ATP (~92 μM for WT-LRRK2 reactions and ~52 μM for G2019S-LRRK2, which represent respective Km ATP concentrations) were added to each reaction, in addition to 0.5 μCi of gamma-32-P-dATP per reaction. Reactions were incubated at 1400 RPM at 30° C. for 30 min. and then spotted in triplicate directly onto a slot-blot apparatus fitted with phospho-cellulose paper and allowed to dry. Each slot was then washed with 10 mM phosphoric acid buffer until beta-radiation could not be detected in eluted wash buffer, usually ~1 mL per slot. Paper within each slot were excised and radiation measured by liquid scintillation. Raw CPM were input into GraphPad, and IC-50 values calculated using non-linear regression analysis, where 100% activity is defined by reactions with control (no) inhibitor compounds, and baseline activity is defined by control reactions that did not include LRRK2 enzyme.

The Table below contains the data for the compounds of the invention.

| Example # | LRRK2 (G2019S) $IC_{50}$ (μM) | Example # | LRRK2 (G2019S) $IC_{50}$ (μM) |
|---|---|---|---|
| 1 | + | 115 | +++ |
| 2 | + | 133 | ++ |
| 3 | +++ | 134 | ++++ |
| 4 | + | 135 | ++++ |
| 5 | +++ | 136 | +++ |
| 6 | +++ | 137 | + |
| 7 | + | 138 | +++ |
| 8 | +++ | 139 | ++ |
| 9 | ++ | 26 | +++ |
| 10 | + | 27 | + |
| 11 | +++ | 28 | + |
| 12 | + | 29 | + |
| 13 | ++ | 30 | + |
| 14 | + | 31 | + |
| 15 | ++ | 32 | + |
| 16 | + | 33 | +++ |
| 17 | + | 34 | ++++ |
| 18 | +++ | 35 | ++ |
| 19 | ++ | 36 | +++ |
| 20 | + | 37 | + |
| 21 | +++ | 38 | + |

-continued

| Example # | LRRK2 (G2019S) $IC_{50}$ (μM) | Example # | LRRK2 (G2019S) $IC_{50}$ (μM) |
|---|---|---|---|
| 22 | + | 39 | + |
| 23 | +++ | 40 | + |
| 24 | +++ | 41 | ++ |
| 25 | ++ | 42 | + |
| 51 | +++ | 43 | + |
| 52 | +++ | 44 | ++ |
| 53 | + | 45 | +++ |
| 54 | +++ | 46 | ++++ |
| 55 | +++ | 47 | +++ |
| 56 | +++ | 48 | +++ |
| 57 | ++ | 49 | +++ |
| 58 | + | 50 | + |
| 59 | + | 77 | + |
| 60 | +++ | 78 | + |
| 61 | + | 79 | ++ |
| 62 | +++ | 80 | +++ |
| 63 | +++ | 81 | +++ |
| 64 | +++ | 82 | + |
| 65 | + | 83 | + |
| 66 | +++ | 84 | + |
| 67 | +++ | 85 | + |
| 68 | + | 86 | + |
| 69 | + | 87 | +++ |
| 70 | + | 88 | ++ |
| 71 | ++ | 89 | +++ |
| 72 | +++ | 90 | ++++ |
| 73 | +++ | 91 | ++ |
| 74 | ++ | 92 | +++ |
| 75 | ++ | 93 | +++ |
| 76 | ++ | 94 | +++ |
| 103 | ++ | 95 | ++ |
| 104 | +++ | 96 | +++ |
| 105 | ++++ | 97 | +++ |
| 106 | +++ | 98 | + |
| 107 | ++ | 99 | + |
| 108 | +++ | 100 | + |
| 109 | +++ | 101 | ++++ |
| 110 | +++ | 123 | ++ |
| 111 | +++ | 124 | +++ |
| 112 | + | 125 | +++ |
| 113 | +++ | 126 | +++ |
| 114 | +++ | | |

+ $IC_{50}$ ≥5 μM,
++ $IC_{50}$ ≥1.0 to <5 μM,
+++ $IC_{50}$ ≥0.1 to <1.0 μM,
++++ $IC_{50}$ <0.1 μM

To test whether Example 90 and Example 34 can inhibit LRRK2 phosphorylation, an antibody commercially available from Epitomics directed against the serine residue number 935 on LRRK2 from lysates generated from HEK-293T cells transiently transfected with either WT-LRRK2 or G2019S-LRRK2 protein. Both Example 90 and Example 34 partially inhibited levels of pS935, which demonstrates that the compounds successfully enter the cells and engage and inhibit LRRK2.

Recently, high levels of LRRK2 expression in primary microglia that are the immune cells of the nervous system have been discovered (Moehle et al., J. Neuroscience (2012), PMID 22302802). This publication shows that knockdown of LRRK2 expression using RNA interference attenuates the induction of the pro-inflammatory and neurotoxic factor TNF-alpha. More recently, LRRK2 has also been detected in primary macrophages, specifically macrophages isolated after thioglycolate exposures in mice. To assess whether Example 90 can inhibit the G2019S-LRRK2 induced increase in TNF-alpha to wild-type levels of TNF-alpha induction by LPS, primary macrophages were exposed in culture to 5 μM 1 hour prior to LPS stimulation (100 ng/ml), and TNF-alpha levels were measured 6 hours later. Example 90 successfully returned G2019S-LRRK2 over-expressing cells back to WT levels, indicating that G2019S-LRRK2 was inhibited in these cells.

In keeping with the present disclosure, the triazolopyridazine compounds of the present disclosure can be used alone or in appropriate association, and also may be used in combination with pharmaceutically acceptable carriers and other pharmaceutically active compounds. The active agent may be present in the pharmaceutical composition in any suitable quantity.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The choice of carrier will be determined in part by the particular method used to administer the composition. Accordingly, there is a wide variety of suitable formulations of the pharmaceutical composition of the present invention. The following formulations for oral, aerosol, parenteral, subcutaneous, intravenous, intraarterial, intramuscular, intraperitoneal, intrathecal, rectal, and vaginal administration are merely exemplary and are in no way limiting.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granule; (c) powders; (d) suspensions in an appropriate liquid; and (e) suitable emulsions. Liquid formulations may include diluents, such as water, cyclodextrin, dimethyl sulfoxide and alcohols, for example, ethanol, benzyl alcohol, propylene glycol, glycerin, and the polyethylene alcohols including polyethylene glycol, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, the addition to the active ingredient in an inert base, such as gelatin and glycerin, or sucrose and acadia, emulsions, and gels containing, in addition to the active ingredient, such carriers as are known in the art.

The triazolopyridazine compounds of the present disclosure alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcelluslose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example. dimethyldialkylammonium halides, and alkylpyridinium halides, (b) anionic detergents such as, for example, alkyl, aryl, and olefin sulfonates, alkyl olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, $4^{th}$ ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

One skilled in the art will appreciate that suitable methods of exogenously administering a compound of the present disclosure to an animal are available, and, although more than one route can be used to administer a particular compound, a particular route can provide a more immediate and more effective reaction than another route.

As regards these applications, the present method includes the administration to an animal, particularly a mammal, and more particularly a human, of a therapeutically effective amount of the compound effective in the inhibition of kinase protein and especially LRRK2. The method also includes the administration of a therapeutically effect amount of the compound for the treatment of patient having a predisposition for being afflicted with Parkinson's disease. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the cancer.

The total amount of the compound of the present disclosure administered in a typical treatment is preferably between about 10 mg/kg and about 1000 mg/kg of body weight for mice, and between about 100 mg/kg and about 500 mg/kg of body weight, and more preferably between 200 mg/kg and about 400 mg/kg of body weight for humans per daily dose. This total amount is typically, but not necessarily, administered as a series of smaller doses over a period of about one time per day to about three times per day for about 24 months, and preferably over a period of twice per day for about 12 months.

The size of the dose also will be determined by the route, timing and frequency of administration as well as the existence, nature and extent of any adverse side effects that might accompany the administration of the compound and the desired physiological effect. It will be appreciated by one of skill in the art that various conditions or disease states, in particular chronic conditions or disease states, may require prolonged treatment involving multiple administrations.

Exemplary embodiments of the present disclosure include:

Embodiment A

A compound represented by formula I:

I

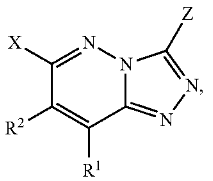

wherein

Z is a 5- or 6-membered substituted or unsubstituted aryl or substituted or unsubstituted heterocyclic ring, each of $R^1$ and $R^2$ is individually selected from the group consisting of hydrogen, halogen, an alkyl group, a substituted or unsubstituted aryl group containing 5 or 6 carbon atoms in the aryl ring;

X is selected from

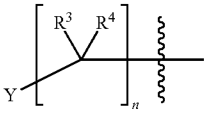

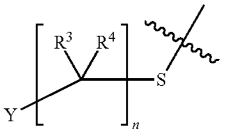

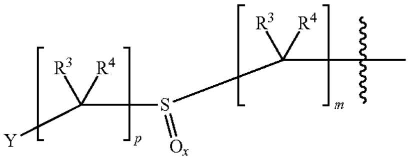

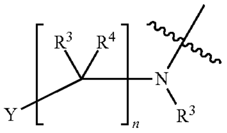

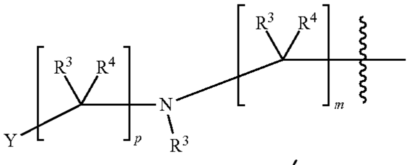

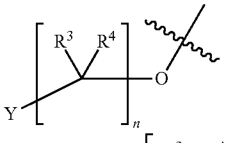

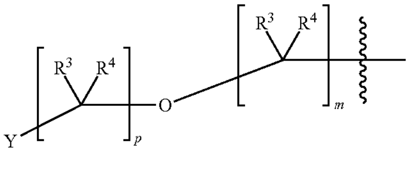

each of $R^3$ and $R^4$ is individually selected from the group consisting of hydrogen, an alkyl group; or $R^3$ and $R^4$ may be combined to form a ring moiety; or $R^3$ and $R^4$ may be combined to form a carbonyl to give a ketone, ester or amide; or either $R^3$ or $R^4$ may be —OH, —O—$R^6$ or —$NH_2$, —$NHR^6$, —$NR^6R^7$, —S—$R^6$ with the proviso that an $R^3$ or $R^4$ does not place two groups selected from —OH, —O—$R^6$ or —$NH_2$, —$NHR^6$, —$NR^6R^7$, —S—$R^6$ on the same C atom; or $R^3$ and $R^4$ may be taken together to form a double or triple bond with the proviso that they are not substituted with a $S(O)_x$, —$NH_2$, —$NH(R^6)$, —$N(R^6R^7)$—, —OH or —O—$R^6$ to give an enol, enolether, vinyl sulfone, vinylthioether, vinylsulfoxide, enamine or the like;

Y may be absent, may be hydrogen, may be substituted or unsubstituted aryl or substituted or unsubstituted heterocyclo group containing 4 to 7 atoms in the ring, or may be $COR^5$ or $S(O)_xR^5$; and $R^5$ is $NH_2$, $NHR^6$, $NR^6R^7$, substituted or unsubstituted aryl or substituted or unsubstituted heterocyclo group containing 4 to 7 atoms in the ring;

m is 1 or 2 n is 1 to 5 p is 0 to 3 x is 0, 1 or 2 each $R^6$ and $R^7$ is individually an alkyl group, an unsubstituted 5- or 6-membered saturated hydrocarbon ring;

or a derivative thereof selected from the group consisting of pharmaceutically acceptable salts, prodrugs, deuterated forms, radio-actively labeled forms, isomers, solvates and combinations thereof Embodiment B A compound according to Embodiment A represented by formula II:

II

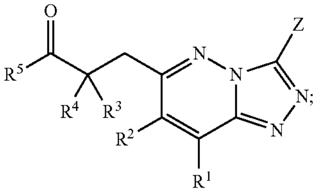

wherein Z, $R^1$ to $R^5$ are as defined above for formula I; or a derivative thereof selected from the group of pharmaceutically acceptable salts, prodrugs, deuterated forms, radio-actively labeled forms, isomers, solvates and combinations thereof.

Embodiment C

A compound according to Embodiment A or B which is selected from the group consisting of:

1-(piperidin-1-yl)-2-((3-(thiophen-2-yl)-[1,2,4]triazolo[4,3-b]pyridazin-6-yl)thio)butan-1-one, 2-((3-(thiophen-2-yl)-[1,2,4]triazolo[4,3-b]pyridazin-6-yl)thio)propanoic acid, 1-(piperidin-1-yl)-2-((3-(thiophen-2-yl)-[1,2,4]triazolo[4,3-b]pyridazin-6-yl)thio)propan-1-one, 1-(azetidin-1-yl)-2-((3-(thiophen-2-yl)-[1,2,4]triazolo[4,3-b]pyridazin-6-yl)thio)propan-1-one, 1-(pyrrolidin-1-yl)-2-((3-(thiophen-2-yl)-[1,2,4]triazolo[4,3-b]pyridazin-6-yl)thio)propan-1-one and 2-(methyl((3-(thiophen-2-yl)-[1,2,4]triazolo[4,3-b]pyridazin-6-yl)methyl)amino)-1-(piperidin-1-yl)propan-1-one, or a derivative thereof.

Embodiment D

A compound according to any one of Embodiments A to C, wherein the isomers are enantiomers or diastereomers.

Embodiment E

A pharmaceutical composition comprising a compound or derivative according to any one of Embodiments A to D and a pharmaceutically acceptable carrier.

Embodiment F

A method of treating a patient with a disease caused by or associated with abnormal LRRK2 kinase activity, which comprises administering to the patient an effective treatment amount of at least one compound, derivative or composition according to any one of Embodiments A to E.

Embodiment G

A method for treating a patient having a neurodegenerative disease, which comprises administering to the patient an effective treatment amount of at least one compound, derivative or composition according to any Embodiments A to E.

Embodiment H

The method according to Embodiment G, wherein the neurodegenerative disease is Parkinson's disease.

Embodiment I

A method for treating a patient suffering from cancer, which comprises administering to the patient an effective treatment amount of at least one compound, derivative or composition according to any one of Embodiments A to E.

Embodiment J

The method according to Embodiment I, wherein said cancer is renal cancer or thyroid cancer.

Embodiment K

A method for treating a patient having an autoimmune disease, which comprises administering to the patient an effective treatment amount of at least one compound, derivative or composition according to any one of Embodiments A to E.

Embodiment L

The method according to Embodiment K, wherein the autoimmune disease is selected from the group consisting of Crohn's disease, rheumatoid arthritis and psoriasis.

Embodiment M

A method for treating a patient having leprosy, which comprises administering to the patient an effective treatment amount of at least one compound, derivative or composition according to any one of Embodiments A to E.

The term "comprising" (and its grammatical variations) as used herein is used in the inclusive sense of "having" or "including" and not in the exclusive sense of "consisting of." The terms "a", "an" and "the" as used herein are understood to encompass the plural as well as the singular, unless indicated otherwise.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A compound selected from the group consisting of 1-(piperidin-1-yl)-2-((3-(thiophen-2-yl)-[1,2,4]triazolo[4,3-b]pyridazin-6-yl)thio)butan-1-one and a derivative of 1-(piperidin-1-yl)-2-((3-(thiophen-2-yl)-[1,2,4]triazolo[4,3-b]pyridazin-6-yl)thio)butan-1-one selected from the group consisting of pharmaceutically acceptable salts, deuterated forms, radio-actively labeled forms, stereoisomers, solvates and combinations thereof.

2. A compound or derivative according to claim 1 wherein the stereoisomers are enantiomers or diastereomers.

3. A compound according to claim 1 which is 1-(piperidin-1-yl)-2-((3-(thiophen-2-yl)-[1,2,4]triazolo[4,3-b]pyridazin-6-yl)thio)butan-1-one.

4. A compound according to claim 1 which is a derivative of 1-(piperidin-1-yl)-2-((3-(thiophen-2-yl)-[1,2,4]triazolo[4,3-b]pyridazin-6-yl)thio)butan-1-one selected from the group consisting of pharmaceutically acceptable salts, deuterated forms, radio-actively labeled forms, stereoisomers, solvates and combinations thereof.

5. A pharmaceutical composition comprising a compound or derivative according to claim 1, and a pharmaceutically acceptable carrier.

6. A pharmaceutical composition comprising the derivative according to claim 4, and a pharmaceutically acceptable carrier.

7. A pharmaceutical composition comprising the compound according to claim 3, and a pharmaceutically acceptable carrier.

* * * * *